(12) United States Patent
Smith et al.

(10) Patent No.: US 11,389,594 B2
(45) Date of Patent: Jul. 19, 2022

(54) ASSEMBLY FOR A MEDICATION DELIVERY DEVICE AND MEDICATION DELIVERY DEVICE

(71) Applicant: NORTON HEALTHCARE LIMITED, Castleford (GB)

(72) Inventors: Christopher James Smith, Prenton (GB); Dale Marc Comley, Parchwich (GB); Lee Thomas Smith, Tixall (GB)

(73) Assignee: NORTON HEALTHCARE LIMITED, Castleford (GB)

( * ) Notice: Subject to any disclaimer, the term of this patent is extended or adjusted under 35 U.S.C. 154(b) by 412 days.

(21) Appl. No.: 16/483,129

(22) PCT Filed: Jan. 25, 2018

(86) PCT No.: PCT/EP2018/051871
§ 371 (c)(1),
(2) Date: Aug. 2, 2019

(87) PCT Pub. No.: WO2018/141633
PCT Pub. Date: Aug. 9, 2018

(65) Prior Publication Data
US 2020/0164153 A1 May 28, 2020

(30) Foreign Application Priority Data
Feb. 3, 2017 (EP) ..................................... 17154626

(51) Int. Cl.
*A61M 5/31* (2006.01)
*A61M 5/315* (2006.01)

(52) U.S. Cl.
CPC ...... *A61M 5/31526* (2013.01); *A61M 5/3146* (2013.01); *A61M 5/3157* (2013.01);
(Continued)

(58) Field of Classification Search
CPC ............ A61M 5/31526; A61M 5/3146; A61M 5/31553; A61M 5/3157;
(Continued)

(56) References Cited

U.S. PATENT DOCUMENTS 5,226,895 A 7/1993 Harris
2006/0270985 A1 11/2006 Hommann et al.
(Continued)

FOREIGN PATENT DOCUMENTS

DE 102004045326 A1 11/2005
EP 0496141 A1 7/1992
(Continued)

*Primary Examiner* — Amber R Stiles
(74) *Attorney, Agent, or Firm* — David S. Safran; Roberts Calderon Safran & Cole, P.C.

(57) ABSTRACT

An assembly for a medication delivery device includes a body, a piston rod, rotatable with respect to the body, for setting a dose of a medication, and axially movable in a distal direction for delivering the set dose, wherein, in cross-section, the piston rod includes a plurality of ratchet teeth to enable rotation of the piston rod during setting of a dose, and a stop member secured against axial and rotational movement, wherein the stop member mechanically cooperates with the piston rod, wherein, when setting the dose, the piston rod becomes aligned with the stop member, and wherein, when delivering the set dose, the piston rod is moved in the distal direction towards the stop member such that the piston rod and the stop member abut at the end of the dose delivery operation and further distal movement of the piston rod is prevented after dose delivery.

20 Claims, 9 Drawing Sheets

(52) U.S. Cl.
 CPC . *A61M 5/31553* (2013.01); *A61M 2005/3126* (2013.01); *A61M 2205/581* (2013.01); *A61M 2205/584* (2013.01)

(58) Field of Classification Search
 CPC .... A61M 2005/3126; A61M 2205/581; A61M 2205/584; A61M 5/3156; A61M 5/3158
 See application file for complete search history.

(56) References Cited

U.S. PATENT DOCUMENTS

| | | |
|---|---|---|
| 2007/0167921 A1 | 7/2007 | Burren et al. |
| 2009/0054846 A1 | 2/2009 | Moser et al. |
| 2010/0010454 A1 | 1/2010 | Marshall et al. |
| 2012/0203184 A1* | 8/2012 | Selz .................. A61M 5/31553 604/207 |
| 2012/0316508 A1 | 12/2012 | Kirchhofer |
| 2015/0250950 A1 | 9/2015 | Moser et al. |
| 2016/0175528 A1 | 6/2016 | Marshall et al. |
| 2016/0367760 A1 | 12/2016 | Bainton et al. |

FOREIGN PATENT DOCUMENTS

| | | |
|---|---|---|
| WO | 9004423 A1 | 5/1990 |
| WO | 2011088894 A1 | 7/2011 |
| WO | 2012118687 A1 | 9/2012 |
| WO | 2016033701 A1 | 3/2016 |

\* cited by examiner

ASSEMBLY FOR A MEDICATION DELIVERY DEVICE AND MEDICATION DELIVERY DEVICE

BACKGROUND OF THE INVENTION

Field of the Invention

The present invention relates to an assembly for a medication delivery device. The present disclosure further relates to a medication delivery device. In particular, the disclosure relates to single-shot variable-dose medication delivery device. The disclosure further relates to a piston rod for a medication delivery device. The piston rod and the assembly may complement each other to work together. The piston rod may be integrated in the assembly and/or the device.

In a single-shot variable-dose medication delivery device, a dose may be delivered with respect to a body of the device in a distal direction by a piston rod. Thereby, the user settable dose of a medication may be expelled from the device. After delivery of the single dose, the device may be locked for preventing a further dose setting or dose delivery operation.

SUMMARY OF THE INVENTION

It is an object of the present invention to provide an assembly for a medication delivery device having improved properties, e.g. increased user comfort, increased safety, lower error-proneness and/or reduced manufacturing costs. Furthermore, it is an object of the disclosure to provide a piston rod for an improved medication delivery device.

This object may be achieved by the subject matter of the independent claims. Advantageous embodiments and refinements are subject matter of the dependent claims.

One aspect relates to an assembly for a medication delivery device. The assembly may be adapted and arranged to be integrated/to be used in the medication delivery device. This means that the assembly may provide specific structural and functional features making the assembly suitable for the medication delivery device. The medication delivery device may be a pen-type device, e.g. a pen-type injector or a pen-type pre-filled syringe.

The medication delivery device may be adapted and arranged to dispense a dose, in particular exactly one dose, i.e. a single dose, of a medication. The device may be a single-shot or single-use device. The medication may be a fluid. The single dose of the medication may be chosen or set by a user. The single dose of medication may, thus, be variable. After delivery of the single dose of the medication, the medication delivery device may be discarded. In particular, further use of the device for setting and dispensing a further dose of the device may be impossible.

The assembly may comprise a body. The body may constitute an outer shell of the assembly or the device. The body may be adapted and arranged to house and protect further components of the assembly or the device. The assembly may comprise a piston rod. The piston rod may be an elongated component adapted and arranged to operate through the body. The piston rod may be adapted and arranged to be rotated with respect to the body for setting a dose of the medication. In other words, the piston rod may be a rotatable component at least during a dose setting operation. As seen in cross-section, the piston rod may comprise a plurality of ratchet teeth. The ratchet teeth may be adapted and arranged to enable rotation of the piston rod during setting of the dose of the medication. By means of the ratchet teeth, the risk of jamming of the piston rod with a further component of the assembly during dose setting, which may, for example occur when the piston rod is provided with a thread, may be reduced or even prevented. Hence, provision of a user-friendly and effective device is facilitated, which is less prone to errors.

The piston rod may be rotatable in only one direction, e.g. the counter-clockwise direction. Rotation of the piston rod in the opposite direction may be prevented. Alternatively, the piston rod may only be one-way-rotational in between a zero dose ("0") and a lowest dose position. Accordingly, the user may be forced to start dialling with the lowest dose of the medication, then increasing the dose up to a maximum. After having dialled the lowest dose, the piston rod may be rotational in both directions, i.e. clockwise and anti-clockwise. This may be especially useful in the case the user dialled too far and then wants to reverse, dialling back down to lower doses.

Preferably, the piston rod is prevented from any axial movement with respect to the body during dose setting. The piston rod may be axially moved in a distal direction with respect to the body for delivering the set dose of the medication. The piston rod may be prevented from being axially moved in the opposite direction, i.e. the proximal direction, with respect to the body during dose delivery.

The assembly may further comprise at least one stop member. The stop member may be secured against axial and rotational movement with respect to the body. The stop member may be adapted and arranged to mechanically cooperate with the piston rod. When setting the dose of the medication, the piston rod may become aligned, e.g. axially and/or azimuthally aligned, with the stop member, in particular with parts or regions of the stop member. In other words, during rotation of the piston rod, the piston rod may be adjusted to a position of the stop member, in particular parts of the stop member. Thus, the dose setting operation may bring the piston rod in a position for mechanically cooperating with the stop member, in particular with specific parts or regions of the stop member.

When delivering the set dose, the piston rod may be moved in the distal direction towards the stop member such that the piston rod and the stop member abut at the end of the dose delivery operation. The piston rod and the stop member abut such that further distal movement of the piston rod may be prevented after the set dose of the medication was delivered, i.e. at the end of the dose delivery operation.

In this way, a distal lock out of the assembly/the device at the end of the dose delivery operation may be provided. Unintentional delivery of a further dose of the medication, which may lead to an underdose, may thus be prevented. Hence, provision of a very safe and user-friendly medication delivery device is facilitated. Moreover, only a minimum number of components is needed for providing the lock out. In particular, the lock out may not increase the number of components. Accordingly, provision of a compact device which is less prone to errors may be facilitated.

According to one embodiment, the at least one stop member is configured such that rotation of the piston rod for setting a further dose of the medication is prevented once the stop member and the piston rod abut after delivery of the set dose. In other words, the stop member may comprise a region, structure, a component and/or a position with respect to the body preventing the piston rod from being rotated for setting a further dose of the medication.

In this way, a rotational lock out at the end of the dose delivery operation may be provided. Unintentional setting of a further dose of the medication may be prevented. This may help to increase the user safety of the device.

According to one embodiment, the at least one stop member comprises a staircase of axial end stops. In one embodiment, the staircase of axial end stops is helically arranged. In particular, the axial end stops may be helically arranged if a difference between selectable doses is in even steps. Accordingly, if, for example, the difference between selectable doses amounts to 0.5, 0.6, 0.7, 0.8, 0.9 etc., the staircase of axial end stops is helically arranged. If the difference between selectable doses is in uneven steps, e.g. 0.5, 0.55, 0.6, 0.8, 0.9, the staircase of axial end stops is not helically arranged.

The respective axial end stop may define the (distal) end of a specific track or path the piston rod may be moved along in the distal direction during dose delivery. An axial position of the respective axial end stop with respect to the body may, thus, determine a distance by which the piston rod is displaceable in the distal direction during dose delivery. Accordingly, the axial position of the respective axial end stop may be directly correlated with the size of the dose delivered from the device.

In this way, provision of a distal end stop may be achieved by simple means. Further components for achieving the distal end stop, which would make the device more complicated, are redundant.

According to one embodiment, the at least one stop member comprises a plurality of rotational end stops. The rotational end stops may comprise different azimuthal/rotational and/or axial positions with respect to the body as compared to one another. The rotational end stops may extend at least partly along a longitudinal axis of the assembly. The rotational stops are "one-sided" rotational stops only. The rotational end stops may be configured to prevent rotation of the piston rod in one direction, e.g. the direction towards the staircase. However, the rotational end stops are not configured to prevent rotation of the piston rod in the direction away from the staircase.

In an alternative embodiment, the rotational end stops of the stop member may be redundant. In this embodiment, the stop member may only comprise the previously mentioned axial end stops.

Axially and/or azimuthally adjacent axial end stops may be connected by one respective rotational end stop. The rotational end stops and the axial end stops may form the previously mentioned staircase. The stop member may, thus, comprise a plurality of structural features, e.g. the axial and rotational end stops. The stop member may be, however, a one-piece component. In this way, provision of a simple and compact device which is less prone to errors may be facilitated.

According to one embodiment, the assembly further comprises an interaction member. The interaction member may comprise a sleeve or tube. The interaction member may be inserted into the body. The interaction member may be an inner sleeve of the body. The interaction member may be secured against axial and rotational movement with respect to the body. The interaction member may be snap-fitted or glued to the body, for example.

The interaction member may comprise the at least one stop member. The stop member may be helically arranged on an inner surface of the interaction member. The stop member, in particular the axial and rotational end stops, may protrude in a radial direction from the inner surface of the interaction member. In other words, the stop member and the interaction member may comprise one single component connected to the body. In this way, provision of a simple and compact device having low manufacturing costs may be facilitated.

In an alternative embodiment, the body may comprise the stop member. The stop member may be helically arranged on an inner surface of the body. The stop member, in particular the axial and rotational end stops, may protrude in a radial direction from the inner surface of the body. In other words, the stop member and the body may comprise one single component. In this embodiment, the interaction member may be superfluous. In this way, manufacturing costs may be reduced and the device may become simpler.

According to one embodiment, the piston rod comprises a contact element. The contact element may comprise a bridge or protrusion protruding from the piston rod. The contact element may be adapted and arranged to mechanically cooperate with a specific axial end stop at the end of the dose delivery operation. In particular, the contact element and the specific axial end stop may abut at the end of the dose delivery operation.

During dose setting, the piston rod may be rotated such that the contact element is brought into alignment, in particular axial and azimuthal alignment, with the specific axial end stop. The contact element and the specific axial end stop may become arranged along the same longitudinal axis.

The respective axial end stop may comprise a specific azimuthal position on the inner surface of the interaction member/body. The azimuthal position of the respective axial end stop with respect to the body may be correlated with a size of the set dose. At the end of the dose setting operation, the piston rod may have been rotated in a specific rotational position with respect to the body correlating with the size of the set dose. The rotational position of the contact element and the azimuthal position of the specific axial end stop may axially overlap at the end of the dose setting operation.

According to one embodiment, the assembly further comprises at least one pawl means, preferably more than one pawl means, e.g. two pawl means. The pawl means may comprise a pawl arm. The pawl means may be secured against axial and rotational movement with respect to the body. The pawl means may be part of the interaction member. Alternatively, the pawl means may be part of the body.

The pawl means and the piston rod may be configured to mechanically cooperate with one another such that, in an unprimed state of the assembly or the medication delivery device, rotation of the piston rod with respect to the body for performing a dose setting operation may be prevented. The unprimed state may be the state of the device when supplied by the manufacturer. When unprimed, rotation of the piston rod may be impossible. Accordingly, the user may be forced to perform a priming operation prior to setting and dispensing the dose of the medication. Thereby, a high dose accuracy can be ensured as any assembly tolerances and/or any air bubble in the cartridge can be removed by performing the priming operation. In this way, dispensal of an underdose, which may have consequences which are detrimental to health for the user, may be prevented. Thus, provision of a safe device with high user comfort is facilitated.

According to one embodiment, the piston rod comprises a first axial region. The first axial region may be the most distal region of the piston rod. The first axial region may be adapted and arranged for a splined engagement with the pawl means in the unprimed state. In this way, rotation of the piston rod in the unprimed state may be effectively prevented.

According to one embodiment, the piston rod comprises an anti-rotation member. The anti-rotation member may comprise a bridge, a rib or a protrusion. Alternatively, the anti-rotation member may comprise a recess or a cut-out. The anti-rotation member may be arranged in the first axial region.

In the unprimed state, the pawl means may engage the anti-rotation member. For this purpose, the pawl means may comprise a recess or cut-out. Alternatively, the pawl means may comprise a bridge, a rib or a protrusion. The pawl means may engage the anti-rotation member such that rotational movement of the piston rod for setting the dose of the medication is prevented. Performing of a dose setting operation as long as the device is unprimed may, thus, be prevented by simple means. For priming the medication delivery device, the piston rod may be moved in the distal direction such that the pawl means and the anti-rotation member are brought out of engagement for enabling rotation of the piston rod for setting the dose of the medication.

According to one embodiment, the stop member may comprise an axial priming stop. The axial priming stop may extend perpendicular to the longitudinal axis. The axial priming stop may be the most proximal structure or feature of the stop member.

The rotational end stops, the axial end stops and the axial priming stop may form the previously mentioned staircase.

In the unprimed state, the contact element and the axial priming stop may be axially aligned. In other words, the contact element and the axial priming stop may be arranged along the same longitudinal axis. During priming, the piston rod, in particular the contact element, may be moved towards the axial priming stop. At the end of the priming operation, the piston rod, in particular the contact element, may abut the axial priming stop such that further distal movement of the piston rod with respect to the body for priming the device may be prevented. Axial priming stop and piston rod may, thus, effectively prevent that the user moves the piston rod too far in the distal direction during the priming operation. Thus, provision of a device which is easy to handle is facilitated.

According to one embodiment, as seen in cross-section, the piston rod may comprise a plurality of ratchet teeth.

The respective ratchet tooth may comprise a distal edge and a proximal edge. The ratchet teeth may be straight. In other words, at least one edge, e.g. the proximal edge, of the respective ratchet tooth may extend substantially perpendicular to the longitudinal axis. In this context, the term "substantially" may mean that it might be desirable to "undercut" the ratchet teeth to increase their strength. The distal edge may be oblique with respect to the longitudinal axis. In particular, the proximal edge may be less oblique than the distal edge. The respective ratchet tooth may extend circumferentially around the piston rod, in particular around a specific region of the piston rod. Axially succeeding ratchet teeth may directly pass over into one another.

The pawl means may be adapted and arranged to mechanically cooperate with the ratchet teeth to provide an audible and/or tactile feedback when the set dose is dispensed from the medication delivery device. Thus, the user knows at any given moment during dose delivery that the set dose is correctly delivered. Moreover, the pawl means may be adapted and arranged to mechanically cooperate with the ratchet teeth to prevent movement of the piston rod in a direction opposite to the distal direction, i.e. in the proximal direction. In this way, provision of a safe and user-friendly device is facilitated.

According to one embodiment, the piston rod comprises a second axial region. The second axial region may be directly adjacent to the first axial region. The first axial region may pass over into the second axial region. The first axial region and the second axial region may be structurally different from one another. The ratchet teeth may extend over the whole length of the second axial region. The respective ratchet tooth extends circumferentially around the second axial region.

According to one embodiment, the piston rod comprises a third axial region. The third axial region may be directly adjacent to the second axial region. The second axial region may pass over into the third axial region. The second axial region may be arranged between the first axial region and the third axial region. The third axial region may be structurally different from the first axial region and from the second axial region.

The contact element may be arranged in the third axial region. The third axial region may be broader, i.e. it may have a greater radial extension, than the first axial region and the second axial region. In this way, mechanical cooperation of the piston rod with the stop member may be facilitated by simple means.

According to one embodiment the assembly further comprises a dose member. The dose member may be adapted and arranged to be rotated with respect to the body for setting the dose of the medication. The dose member may be gripped for being rotated by the user. The dose member may be adapted and arranged to be axially moved in the distal direction with respect to the body for delivering the set dose of the medication. The dose member may be tubular. The piston rod may be coupled to the dose member such that relative axial and rotational movement of the piston rod and the dose member is prevented. Alternatively, the piston rod and the dose member may be integrally formed. This means that the piston rod and the dose member may constitute one single, e.g. injection moulded, component of the device.

According to one embodiment, the ratchet teeth may extend circumferentially around the piston rod.

According to one embodiment, the assembly may further comprise an interaction member secured against axial and rotational movement with respect to the body, wherein the interaction member comprises the at least one stop member and pawl means which are configured to mechanically cooperate with the piston rod. The interaction member may comprise two pawl means. The pawl means may be arranged opposite to each other.

The stop member may be secured against axial and rotational movement with respect to the body. The stop member may be adapted and arranged to mechanically cooperate with the piston rod. When setting the dose of the medication, the piston rod may become aligned, e.g. axially and/or azimuthally aligned, with the stop member, in particular with parts or regions of the stop member. In other words, during rotation of the piston rod, the piston rod may be adjusted to a position of the stop member, in particular parts of the stop member. Thus, the dose setting operation may bring the piston rod in a position for mechanically cooperating with the stop member, in particular with specific parts or regions of the stop member.

When delivering the set dose, the piston rod may be moved in the distal direction towards the stop member such that the piston rod and the stop member abut at the end of the dose delivery operation. The piston rod and the stop member abut such that further distal movement of the piston rod may be prevented after the set dose of the medication was delivered, i.e. at the end of the dose delivery operation.

According to a further aspect, a medication delivery device is described. The medication delivery device may comprise the previously described assembly. The assembly may be integrated in the device or may be part of the device. The device may be a single-shot variable-dose device. In particular, the device may be adapted for dispensing a single, user-variable dose.

The medication delivery device may comprise a cartridge. The cartridge may comprise a medication which is dispensed in a (single) dose delivery operation by the assembly. Alternatively, the medication delivery device may be a syringe, in particular a pre-filled syringe, comprising the medication which is dispensed in the (single) dose delivery operation by the assembly.

The device may be supplied to the user in an unprimed state. Before the device is in a condition for setting the single dose of the medication, the user may have to prime the device. After delivery of the single dose of the medication, the device may be locked such that a further dose setting and dose delivery operation may be prevented. In this way, a user-friendly and safe device is provided which has a low number of components.

According to a further aspect, a piston rod for a medication delivery device is described. The piston rod may be adapted and arranged to be integrated in the previously described assembly or device. The piston rod may comprise a distal end and a proximal end. The distal end may be that end of the piston rod which is arranged closest to a dispensing end of the device once the piston rod has been assembled to the device. The piston rod may be a rotatable component once integrated in the device. In particular, the piston rod may be rotatable for/during dose setting.

According to one embodiment, the piston rod, in particular a region thereof, comprises a plurality of cone-shaped segments. In particular, the respective segment may comprise the shape of a truncated cone. A bottom surface of the respective segment may comprise a greater diameter than a top surface. The bottom surface may constitute the proximal surface of the respective segment. The top surface may constitute the distal surface of the respective segment. Said segments may be stacked above one another in an axial direction.

As seen in cross-section, the segments may constitute a plurality of ratchet teeth extending along the piston rod, in particular along a specific region of the piston rod. In other words, in cross-section, the piston rod may comprise a plurality of straight ratchet teeth extending at least partly along the piston rod. The ratchet teeth may extend circumferentially around the piston rod, in particular around the specific region of the piston rod.

An edge, e.g. the proximal edge, of the respective ratchet tooth may extend perpendicular to a longitudinal axis of the piston rod. The proximal edge may correspond to a part of the bottom surface of the respective segment. A further edge, e.g., the distal edge, of the respective ratchet tooth may be oblique with respect to the longitudinal axis. The distal edge may, thus, be less steep than the proximal edge. The distal edge may correspond to a side surface of the respective segment. The proximal edge of one of the respective ratchet teeth may directly pass over into the distal edge of the (proximally) adjacent ratchet tooth.

According to one embodiment, the piston rod comprises a first axial region. The piston rod may comprise a second axial region. The piston rod may comprise a third axial region. The three axial regions may pass over into one another as seen along the longitudinal axis of the piston rod. The piston rod may be a single-piece component.

The second axial region may be arranged between the first axial region and the third axial region. The three axial regions may be structurally different from one another. A diameter of the second axial region may be smaller than the diameter of the first axial region and the third axial region. The segments and, thus, the ratchet teeth may be arranged in the second axial region. The respective ratchet tooth may extend circumferentially around the second axial region.

The first axial region may comprise a distal end. The distal end of the first region may be shaped plate-like. Moreover, the first region may comprise at least one anti-rotation member, e.g. two anti-rotation members. The anti-rotation member may be adapted and arranged to prevent the rotation of the piston rod in an unprimed state. The anti-rotation member may be arranged in the proximal end section of the first region. The proximal end section of the first region may be cone-shaped. In particular, the proximal end section of the first axial region may comprise the shape of a truncated cone. The anti-rotation member may comprise an elevation which protrudes from a side surface of the cone-shaped proximal end section in the radial direction. Alternatively, the anti-rotation member may comprise a recess or groove arranged in the side surface of the proximal end section.

The first axial region may further comprise a middle section arranged between the distal end and the proximal end section. The middle section may be segmented. The middle section may comprise axially extending segments or struts which extend along a longitudinal axis of the piston rod.

The third axial region may be shaped plate-like. The third axial region may comprise a contact element. The third axial region may comprise a plurality of contact elements. In this way, strength/balance forces may be increased. The contact element may comprise a protrusion protruding radially from an outer surface, in particular an edge, of the third region. The contact element may be shaped rectangularly. Of course, other shapes of the contact element are possible, e.g. a rounded shape.

The third axial region may further comprise at least one, preferably two, engagement features. The respective engagement feature may be arranged on the proximal end, in particular on the proximal surface, of the third axial region. The respective engagement feature may comprise a protrusion which extends in the proximal direction. An end-face of the respective engagement feature may be arcuate.

The piston rod may be a multifunctional component. Once integrated into the device/complemented with the assembly, the piston rod may, in interaction with further components, help to
- establish a prime lock such that setting of a dose is prevented in the unprimed state,
- provide a distal lock out after priming such that "overpriming" is prevented,
- create a user feedback during dose delivery,
- establish a final lock out after dose delivery.

In this way, provision of a device is facilitated which is very safe and, moreover, easy to handle.

In the following text, a set of advantageous aspects is described. The aspects are numbered to facilitate referencing features of one aspect in other aspects. Features from the aspects are not only relevant in connection with the specific aspects they relate to but are also of relevance on their own.

The following aspects relate to a specifically designed dose member comprising tracks with different sections which enable the setting of discrete doses by rotation of the dose member and/or a rotational lock out of the dose member and, thus, of the device during dose delivery. In this way, provision of a device with high user comfort and high safety is facilitated.

The aspects discussed in the following refer to embodiments wherein the tracks with the different sections are provided by the dose member. The dose member may constitute the piston rod or a part of the piston rod of the assembly/the device. Alternatively, the dose member may be a component separate from the piston rod. The tracks may be adapted for mechanical cooperation with at least one deflectable feature, preferably two deflectable features. The said deflectable feature may be provided by the body. However, in alternative embodiments, the deflectable feature may be provided by an inner sleeve of the body, e.g. the interaction member. The deflectable feature may be part of a component which is secured against axial and rotational movement with respect to the body. Alternatively, the tracks and the deflectable feature may be reversed. Accordingly, the deflectable feature may be part of a component which is axially and/or rotationally moveable with respect to the body. For example, the tracks could run down the inside of the body/the interaction member and the deflectable feature could be located on the piston rod.

The set of following set aspects comprises subject matters which may comprise any structural and functional feature described above.

1. An assembly for a medication delivery device comprising
    a body,
    a dose member adapted and arranged to be rotated with respect to the body for setting a dose of a medication and to be axially moved in a distal direction with respect to the body for delivering the set dose of the medication, wherein the dose member comprises a plurality of tracks extending at least partly along an outer surface of the dose member, wherein the respective track comprises a first section and a second section,
    at least one deflectable feature which is secured against axial and rotational movement with respect to the body, wherein the deflectable feature is adapted and arranged to mechanically cooperate with the tracks of the dose member,
    wherein during dose setting, the deflectable feature is adapted and arranged to mechanically cooperate with the first section of various tracks and during dose delivery, the deflectable feature is adapted and arranged to mechanically cooperate with the second section of one specific track.
2. The assembly according to aspect 1,
    wherein an azimuthal position of the respective track with respect to the body correlates with the size of the set dose.
3. The assembly according to aspect 1 or aspect 2,
    wherein an azimuthal position of the respective track corresponds to a discrete dose set and dispensed from the device.
4. The assembly according to any of the previous aspects,
    wherein the deflectable feature is radially deflectable with respect to the body.
5. The assembly according to any of the previous aspects,
    wherein the deflectable feature comprises a deflectable detent.
6. The assembly according to any of the previous aspects,
    wherein the first section of the respective track passes directly over into the second section of the respective track as seen along a longitudinal axis of the dose member.
7. The assembly according to any of the previous aspects,
    wherein the first section comprises an outer shape which is overridable by the deflectable feature and wherein the second section comprises an outer shape which is non-overridable by the deflectable feature.
8. The assembly according to any of the previous aspects,
    wherein the first section of the respective track comprises side walls which are rounded and wherein the second section of the respective track comprises side walls which are edged.
9. The assembly according to any of the previous aspects,
    wherein side walls of the respective second section extend perpendicular to a longitudinal axis of the dose member and wherein side walls of the respective first section are oblique with respect to the longitudinal axis.
10. The assembly according to any of the previous aspects,
    wherein the second section is deeper than the first section.
11. The assembly according to any of aspects 8 to 10,
    wherein for setting the dose of the medication, the dose member is rotated such that the deflectable feature slides from the first section of a respective track over the side wall of the first section and into the first section of an azimuthally adjacent track.
12. The assembly according to any of the previous aspects,
    wherein at the end of the dose setting operation, the deflectable feature mechanically cooperates with the first section of the specific track correlating with the size of the set dose.
13. The assembly according to any of the previous aspects,
    wherein for delivering the set dose, the dose member is moved in the distal direction such that the deflectable feature passes over from the first section and into the second section of the specific track, wherein mechanical cooperation of the deflectable feature and the second section prevents rotation of the dose member for setting a further dose of the medication.
14. The assembly according to any of the previous aspects,
    wherein the deflectable feature is part of the body or is connected to the body.
15. A medication delivery device comprising the assembly according to any of the previous aspects, wherein the device is a single-shot variable-dose device.
16. The medication delivery device according to aspect 15,
    wherein either the medication delivery device comprises a cartridge comprising a medication which is dispensed in a dose delivery operation by the assembly or the medication delivery device is a syringe comprising a medication which is dispensed in a dose delivery operation by the assembly.

Features which are described herein above and below in conjunction with different aspects or embodiments, may also apply for other aspects and embodiments. Further aspects, features and advantages of the present invention will be apparent from the following description of preferred embodiments with reference to the accompanying drawings.

DETAILED DESCRIPTION OF THE INVENTION

Figure 1:
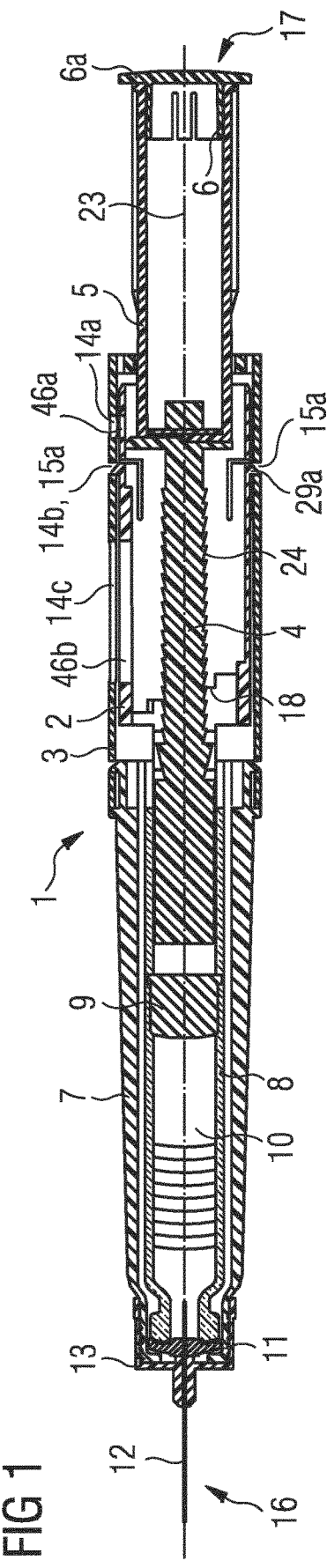
FIG. 1 schematically shows a sectional side view of a medication delivery device according to a first embodiment, FIG. 2 schematically shows a perspective view of the medication delivery device of FIG. 1, FIG. 3 schematically shows a sectional side view of parts of a medication delivery device according to a second embodiment, FIG. 4 schematically shows an exploded view of the medication delivery device of FIG. 1, FIG. 5 schematically shows a sectional side view of the medication delivery of FIG. 1 as supplied from the manufacturer, FIG. 6 schematically shows a sectional side view of the medication delivery of FIG. 1 after a priming operation, FIG. 7 schematically shows a sectional side view of the medication delivery of FIG. 1 after a dose setting operation, FIG. 8 schematically shows a sectional side view of the medication delivery of FIG. 1 after a dose delivery operation, FIG. 9 schematically shows a perspective view of a component, in particular the interaction member, of the medication delivery device according to FIG. 1 or 3, FIG. 10 schematically shows a perspective view of a further component, in particular the piston rod, of the medication delivery device according to FIG. 1 or 3, FIG. 11 schematically shows a perspective view of a further component, in particular the dose member, of the medication delivery device according to FIG. 1 or 3, and FIG. 12 schematically shows a perspective view of a further component, in particular the body, of the medication delivery device according to FIG. 1 or 3.

Like elements, elements of the same kind and identically acting elements may be provided with the same reference numerals in the figures.

Figure 2:
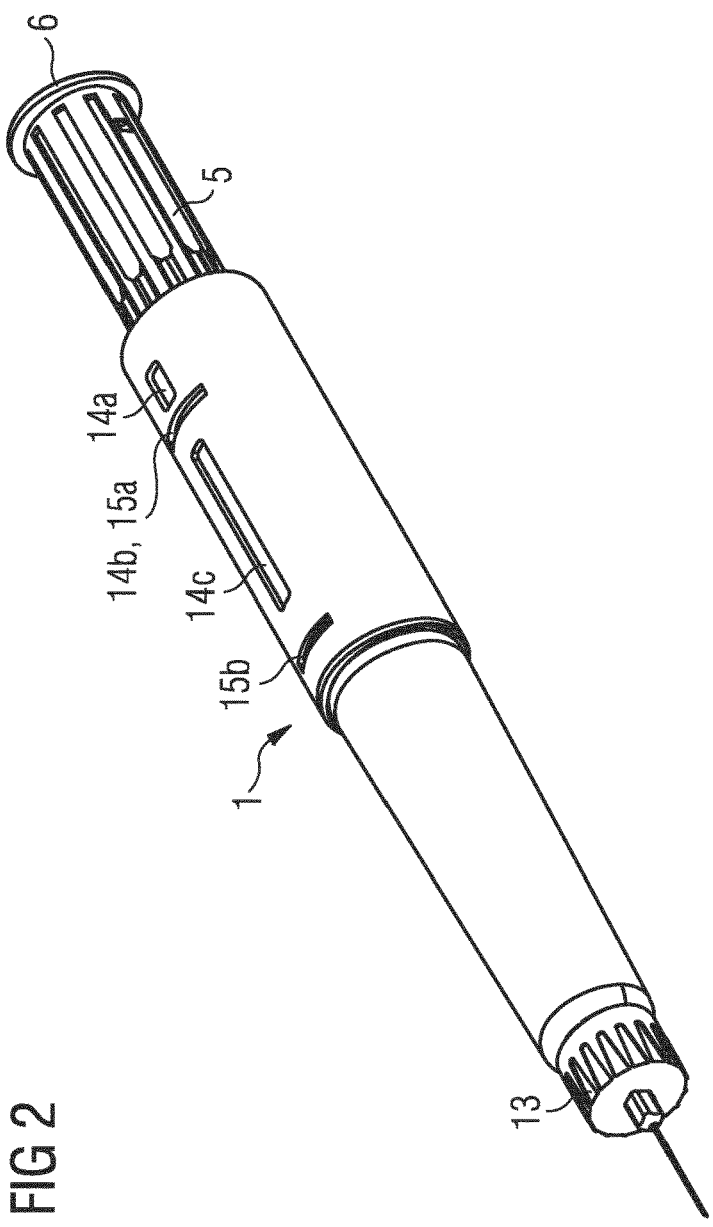
Figure 3:
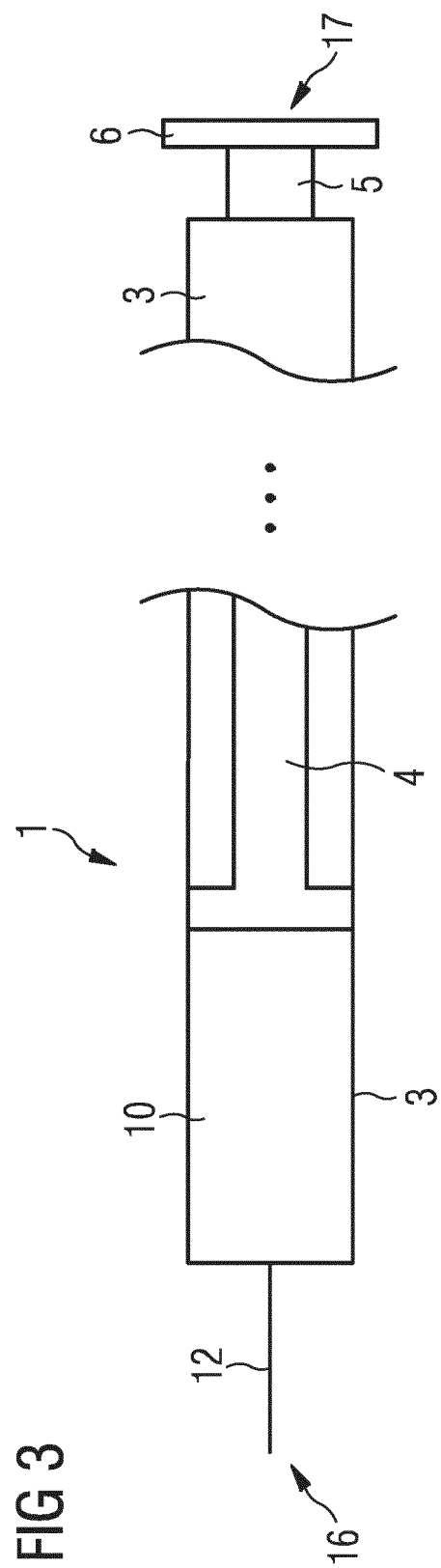

In FIGS. 1 to 4 a medication delivery device 1 is shown. The medication delivery device 1 comprises a body 3 (see also FIG. 12). The body 3 may be designed to enable a safe and comfortable handling of the medication delivery device 1. The body 3 may be configured to house, fix, protect and guide inner components of the medication delivery device 1, e.g. a piston rod 4, a dose member 5 and/or an interaction member 2 which are described below in detail. Preferably, the body 3 limits or prevents the exposure of the inner components and/or a medication 10 to contaminants such as liquid, dirt or dust. The body 3 may be a unitary or a multipart component. The body 3 may comprise a tubular or a cylindrical shape, as shown in FIGS. 2 and 3, for example. Alternatively, the body 3 may comprise a non-tubular shape.

The medication delivery device 1 and the body 3 have a distal end 16 and a proximal end 17. The distal end 16 designates that end of the device 1 or a component thereof which is or is to be arranged closest to a dispensing end of the medication delivery device 1. The proximal end 17 designates that end of the device 1 or a component thereof which is or is to be arranged furthest away from the dispensing end of the medication delivery device 1.

The medication delivery device 1 is adapted and arranged to retain a medication 10, preferably one dose of the medication 10. The medication delivery device 1 may be adapted and arranged to delivery one dose of a single medication 10. This means that no mixing of different medications 10 may occur before delivering the dose of the medication 10.

The medication 10 is preferably a liquid. The device 1 may be a one-shot variable dose device. This means that the device 1 may be intended for a single use, i.e. for dispensing only one dose of the medication 10. After delivery of said dose of the medication 10, the device 1 may be discarded. The size of said dose of medication 10 may be settable by a user, i.e. it is a variable dose.

In one embodiment, the medication delivery device 1 comprises a cartridge 8 for holding the medication 10 (see, for example, FIG. 1). The cartridge 8 is a single chamber cartridge. In this embodiment, the cartridge 8 can be retained within a cartridge holder 7 (see FIG. 1). The cartridge holder 7 may be configured for stabilizing the cartridge 8 mechanically. The cartridge holder 7 may be connected to the body 3. In a further embodiment, no cartridge holder 7 may be provided and the cartridge 8 may be connected directly to the distal end of the body 3.

The cartridge holder 7 or the cartridge 8 may be non-releasably connected, e.g. snap-fitted or screwed, to the body 3. The cartridge 8 or the cartridge holder 7 may be connected to the body 3 such that relative axial and rotational movement of the cartridge 8/cartridge holder 7 and the body 3 is prevented. For this purpose, the body 3 may comprise a coupling member 15*b* (FIG. 4), e.g. a slot, a recess, a rib or a protrusion, and the cartridge 8 or the cartridge holder 7 may comprise a mating coupling member 47 (see FIG. 4).

In an alternative embodiment, the body 3 may be adapted and arranged to house and protect the medication 10. In this case, the medication 10 may be retained directly within an interior of the body 3, in particular in a specific section or region, e.g. the most distal region, of the body 3. The body 3 may be a one-piece component holding the medication 10. Accordingly, a cartridge for retaining the medication 10 and a cartridge holder may be superfluous. In this embodiment, the medication delivery device 1 is supplied and designed as a pre-filled syringe as can be gathered from FIG. 3.

The cartridge 8 or the body 3 may comprise an outlet. The medication 10 can be dispensed from the cartridge 8 or the body 3 through said outlet. A septum 11 (see FIGS. 1 and 4) may seal the outlet. The septum 11 may be made of an elastically deformable material. The device 1 further comprises a needle assembly 13. The needle assembly 13 may be connected, e.g. screwed, to the distal end of the cartridge holder 7/the cartridge 8 or the body 3. By means of the needle assembly 13 a needle 12 may be secured to the device 1. The septum 11 may be pierceable by the needle 12 for dispensing the set dose of the medication 10 via the needle 12 extending through the outlet.

The medication delivery device 1 further comprises the previously mentioned piston rod 4. The piston rod 4 may be an injection moulded component. The piston rod 4 is adapted and arranged to operate through the body 3 of the device 1. The piston rod 4 is designed to transfer axial movement through the medication delivery device 1, for example for the purpose of delivering the set dose of the medication 10. The piston rod 4 is rotatable with respect to the body 3 for setting the dose of the medication 10. In one embodiment, the piston rod 4 may be rotational in only one rotational direction, e.g. in the anti-clockwise direction when viewing from the proximal end towards the distal end. This rotational direction is in the following referred to as the rotational direction of the piston rod 4.

In a preferred embodiment, the piston rod 4 is only one-way-rotational in between the "0" and "lowest dose" position. Accordingly, the user may be forced to start dialling with the lowest dose of the medication 10, then increasing the dose up to the maximum. After having dialled the "lowest dose", the piston rod 4 may be rotational in both directions, i.e. clockwise and anti-clockwise. This may be especially useful in the case the user dialled too far and then wants to reverse, dialling back down to lower doses.

The piston rod 4 is axially, in particular distally, moveable with respect to the body for delivering the set dose of the medication 10. For dose delivery, the piston rod 4 is moved along a longitudinal axis 23 of the device 1. During dose delivery, rotation of the piston rod 4 with respect to the body 3 is prevented. Moreover, throughout operation of the device 1, movement of the piston rod 4 in the proximal direction is prevented. These features are described later on in detail.

The device 1 comprises a dose 9 (see FIG. 1). The dose 9 may be slideably retained within the cartridge 8 or the body 3 of the device 1. Preferably, the dose 9 comprises a resilient material. The dose 9 may seal the cartridge 8 or the section of the body 3 containing the medication 10 proximally. The dose 9 is movable with respect to the cartridge 8 or the body 3. In particular, axial movement of the piston rod 4 for delivering the set dose may be transferred to the dose 9. Movement of the dose 9 in the distal direction with respect to the body 3 causes the set dose of the medication 10 to be dispensed from the device 1 through the outlet.

Figure 10:
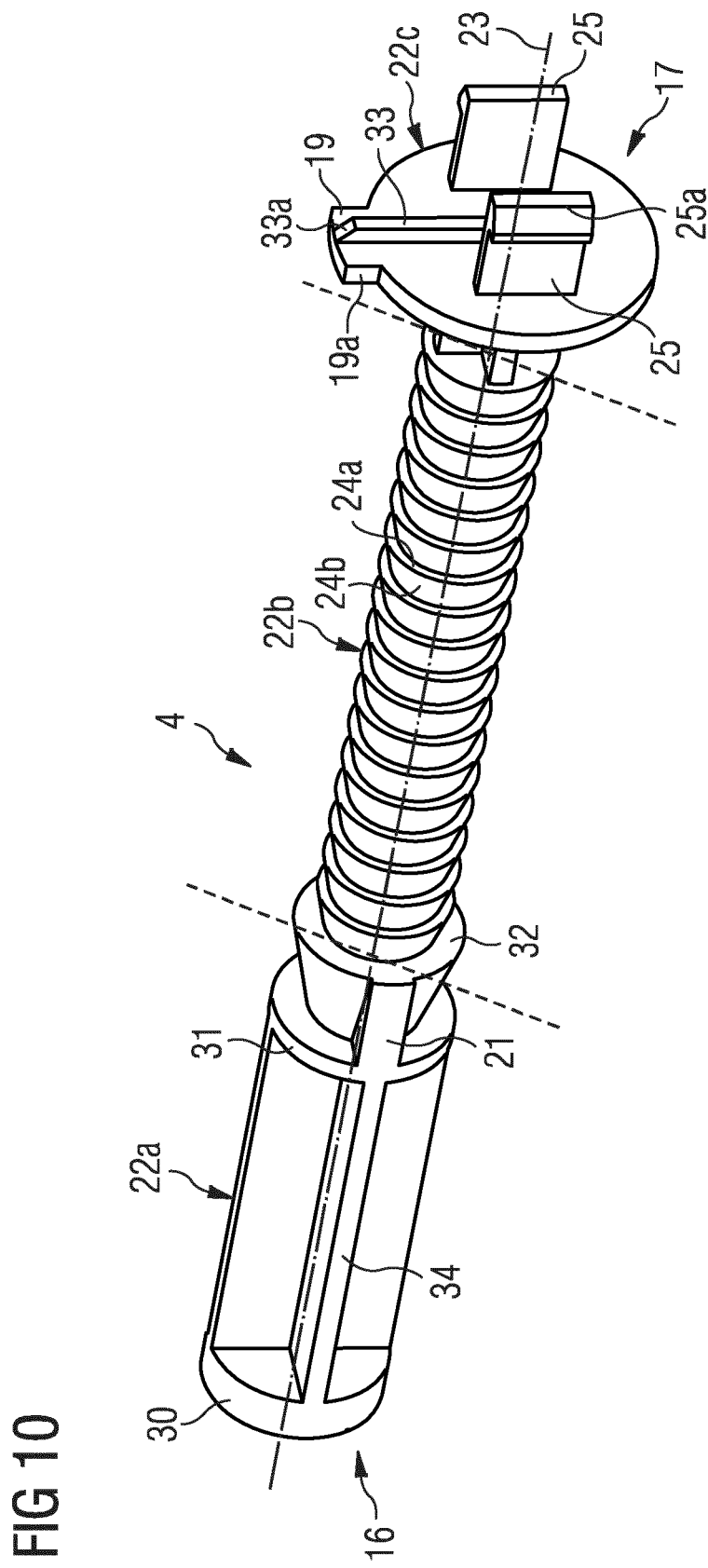

The piston rod 4 comprises a first axial region 22a, a second axial region 22b and a third axial region 22c as can be gathered from FIG. 10. The respective axial region 22a, 22b, 22c extends along the longitudinal axis 23. The regions 22a, 22b, 22c pass over into one another. In particular, the piston rod 4 is integrally formed which means that the piston rod 4 is a one-piece component. A transition area between adjacent regions 22a, 22b, 22c is indicated by the dashed lines in FIG. 10. The first region 22a is the most distal region, i.e. it is arranged closest to the dispensing end of the device 1. The third region 22c is the most proximal region, i.e. it is arranged furthest away from the dispensing end. The second region 22b is arranged between the first and the third region 22a, 22c. The regions 22a, 22b, 22c comprise different outer shapes, structures and functions as compared to one another.

The first region 22a comprises a distal end 30. The distal end 30 of the first region 22a is shaped plate-like. The distal end 30 is adapted and arranged for mechanical cooperation with the previously mentioned dose 9 of the device 1. Moreover, the first region 22a comprises at least one anti-rotation member 21. In this embodiment, two anti-rotation members 21 are provided. The respective anti-rotation member 21 is adapted and arranged to prevent the rotation of the piston rod 4 in an unprimed state of the device 1. This is described later on in connection with the description of the working principle of the device 1.

The anti-rotation member 21 is arranged in the proximal end section of the first region 22a. The proximal end section of the first region 22a is cone-shaped. In particular, the proximal end section of the first axial region 22a comprises the shape of a truncated cone. The respective anti-rotation member 21 comprises an elevation which protrudes from a side surface of the cone-shaped proximal end section in the radial direction. Alternatively, the anti-rotation member 21 may comprise a recess or groove arranged in the side surface of the proximal end section.

The two anti-rotation members 21 are oppositely arranged with respect to the longitudinal axis 23. In cross-section, the anti-rotation members 21 are shaped triangularly or ramp-like. An outer surface or top surface of the respective anti-rotation member 21 extends along the longitudinal axis 23. A distal surface of the respective anti-rotation member 21 extends perpendicular to the longitudinal axis 23. The outer surface and the distal surface are connected by an oblique surface extending along the cone-shaped proximal end section of the first region 22a.

In this context, it should be noted that the anti-rotation member 21, in particular the two elevations are integrally formed with the piston rod 4, in particular with the first region 22a. As seen in the distal direction, the proximal end section of the first region 22a is succeeded by a plate. In other words, in the distal direction, the anti-rotation member 21 is confined by a plate-like structure 31. This plate-like structure 31 constitutes a stop collar enabling abutment of the piston rod 4 and a further component (e.g. a pawl means 20) in an unprimed state of the device 1. Again this is described later on in detail.

The first region 22a finally comprises a middle section arranged between the distal end 30 and the plate-like structure 31. The middle section is segmented. In particular, it comprises four axially extending segments or struts 34 which extend along the longitudinal axis 23. As seen in cross-section, the middle section is cross-shaped. This is a good shape for stability and material strength (and also for moldability). However, other shapes are also possible (e.g. an annulus cross-section, formed by a mold tool "core pin" inserted from the distal end).

The distal end of the middle section is terminated by the plate like distal end 30 of the first region 22a. The proximal end of the middle section is terminated by the plate-like structure 31. By means of the segmented middle section of the first region 22a, the stability of the piston rod 4 is increased. Furthermore, the material costs are reduced.

As seen in the proximal direction, the first region 22a passes over into the second region 22b. In a transition region between the second region 22b and the first region 22a a plate-like structure 32 is provided. The plate like structure 32 constitutes a proximal end face of the proximal end section of the first region 22a. The plate like structure 32 constitutes a bottom surface of the truncated cone.

In the shown embodiment, the second axial region 22b is less broad than the first axial region 22a. In other words, the first axial region 22a has a greater radial extension or diameter than the second axial region 22b. However, provided that both the first axial region 22a and the second axial region 22b can fit inside an inner diameter of the cartridge 8, and that both regions 22a, 22b are structurally stable, the axial regions 22a, 22b may also have the same diameter or the second axial region 22b may be broader than the first axial region 22a.

The second region 22b is structured. The second axial region 22b comprises a plurality of segments. The respective segment comprises the shape of a truncated cone.

The segments are stacked above one another as seen along the axial direction. The proximal end of the respective segment is broader than the distal end. In other words, the distal or top surface of the respective segment comprises a smaller diameter than the proximal or bottom surface. Distal surface and proximal surface are connected via an oblique side surface of the respective segment.

In cross-section, the previously described segments constitute a plurality of ratchet teeth 24 (see FIG. 1). The ratchet teeth 24 extend along the whole second axial region 22b. The teeth 24 extend circumferentially around the piston rod 4, respectively. The ratchet teeth 24 are straight. This means a proximal edge 24a of the respective ratchet tooth 24 (corresponds to a fraction of the proximal surface of the respective segment) extends perpendicular to the longitudinal axis 23. A distal edge 24b of the respective ratchet tooth 24 (corresponds the side surface of the respective segment) is oblique with respect to the longitudinal axis 23.

The ratchet teeth 24 pass over into one another. In other words, the proximal edge 24a of a first ratchet tooth 24 is directly followed by/passes over into the distal edge 24b of a second ratchet tooth succeeding the first ratched tooth 24 in the proximal direction. The structured second region 22b enables rotation of the piston rod 4 during setting of a dose of the medication 10.

As seen in the proximal direction, the second region 22*b* passes over into the third axial region 22*c*. The third axial region 22*c* is broader than the first axial region 22*a* and the second axial region 22*b*. In particular, the third region 22*c* comprises a radial extension which is greater than the radial extension of the first region 22*a* and the second region 22*b*. The third region 22*c* is shaped plate-like. The piston rod 4, in particular the third region 22*c* comprises a contact element 19. The piston rod 4 may comprise a plurality of contact elements 19. In this way, strength/balance forces may be increased. For example, two contact elements 19 may be arranged at 180°. The two contact elements 19 would have to be combined with duplicate sets of staircase stops 18*a*, which are described later on in detail.

The contact element 19 comprises a protrusion protruding radially from an outer surface, in particular an edge, of the third region 22*c*. The contact element 19 emerges from the side edge of the plate-like third axial region 22*c* in the radial outward direction. The contact element 19 constitutes a confined/limited extension of the third region 22*c* towards the radial direction. The contact element 19 is shaped rectangularly. Of course, other shapes of the contact element 19 are possible, e.g. a rounded shape. The contact element 19 is formed integrally with the piston rod 3, in particular with the third region 22*c*.

The third region 22*c* comprises two engagement features 25. The respective engagement feature 25 is arranged on the proximal end, in particular on the proximal surface, of the third region 22*c*. The respective engagement feature 25 comprises a protrusion which extends in the proximal direction. An end-face 25*a* of the respective engagement feature 25 is arcuate. In other words, the respective engagement feature 25 is shaped like a hook for enabling engagement, in particular non-releasable engagement, with a dose member 5 of the device 1.

The third region 22*c* further comprises a guide member 33. The guide member 33 is arranged on the proximal surface of the third region 22*c*. The guide member 33 comprises a protrusion which extends from the proximal surface in the proximal direction. The guide member 33 is arranged between the two engagement features 25. The guide member 33 extends from an edge of the third region 22*c*, in particular an edge of the contact element 19, towards a middle region of the proximal surface. The guide member 33 is shaped bar-like. An outer edge 33*a* or end-face of the guide member 33 is oblique with respect to the longitudinal axis 23. The guide member 33 is adapted and arranged to align the piston rod 4 with the dose member 5 when the piston rod 4 and the dose member 5 are connected to one another and to transfer rotation of the dose member 5 to the piston rod 4 during dose setting.

Figure 11:
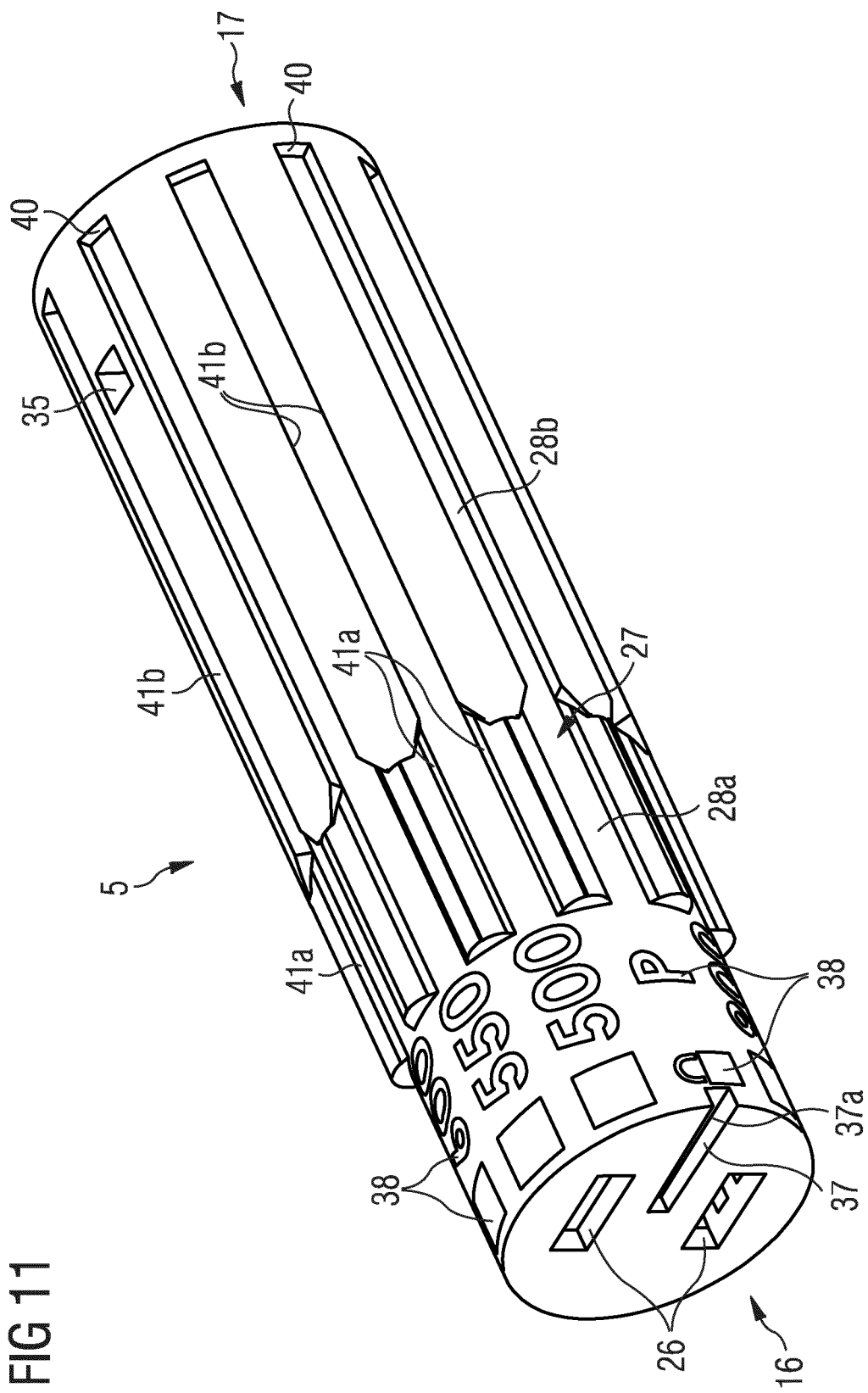

The medication delivery device 1 further comprises the previously mentioned dose member 5 (see, in particular, FIG. 11). The dose member 5 is arranged at least partly within the body 3 as can be gathered from FIGS. 1 to 3. The dose member 5 is tubular shaped. The dose member 5 is rotatable with respect to the body 3 for setting the dose of the medication 10. For setting the dose, the dose member 5 is rotatable in the previously defined rotational direction. The dose member 5 may be permitted to be rotated in a direction opposite to the rotational direction (e.g. to the counterclockwise direction) to dial back down to select a lower dose in case the user dialled too far.

The dose member 5 is axially moveable in the distal direction with respect to the body 3 for delivering the set dose. The dose member 5 and the piston rod 4 are coupled, in particular non-releasably connected, to one another. For example, piston rod 4 and dose member 5 are snap-fitted to one another. In this way, relative axial and rotational movement of the dose member 5 and the piston rod 4 is prevented.

For this purpose, the piston rod 4 comprises the previously described engagement features 25 (see FIG. 10). The dose member 5 comprises mating engagement features 26 (FIG. 11). The two mating engagement features 26 are arranged on a distal surface of the dose member 5. The mating engagement features 26 comprise recesses. The hook-shaped engagement features 25 are inserted into the mating engagement features 26 for non-releasably connecting the piston rod 4 and the dose member 5. For aligning the dose member 5 and the piston rod 4 and, thus, facilitating the connection of the two components, the previously described guide member 33 of the piston rod 4 is thereby inserted into a mating guide member 37, e.g. a recess of the dose member 5. The mating guide member 37 is arranged on the distal surface of the dose member 5 between the two mating engagement features 26. The mating guide member 37 comprises an open end 37*a*.

In an alternative embodiment, the dose member 5 and the piston rod 4 may be integrally formed. In other words, the piston rod 4 and the dose member 5 may constitute one single component of the device 1. In this embodiment, piston rod 4 and dose member 5 may be injection moulded as one piece. In this embodiment, the previously described engagement features 25, 26 and the guide members 33, 37 may be redundant.

The dose member 5 further comprises an open proximal end 17. In the open proximal end 17, an end cap 6 (see FIGS. 1 and 4) is inserted. The end cap 6 constitutes a proximal closure of the dose member 5. The end cap 6 comprises an outer or proximal surface 6*a*. The outer surface 6*a* is adapted and arranged to be pushed by the user for delivering the set dose of the medication 10. The end cap comprises a distal section. The distal section is shaped sleeve-like or tubular-like. The distal section comprises a side wall. The distal section is completely arranged within the dose member 5 once the dose member 5 and the end cap 6 have been connected to one another.

Figure 4:
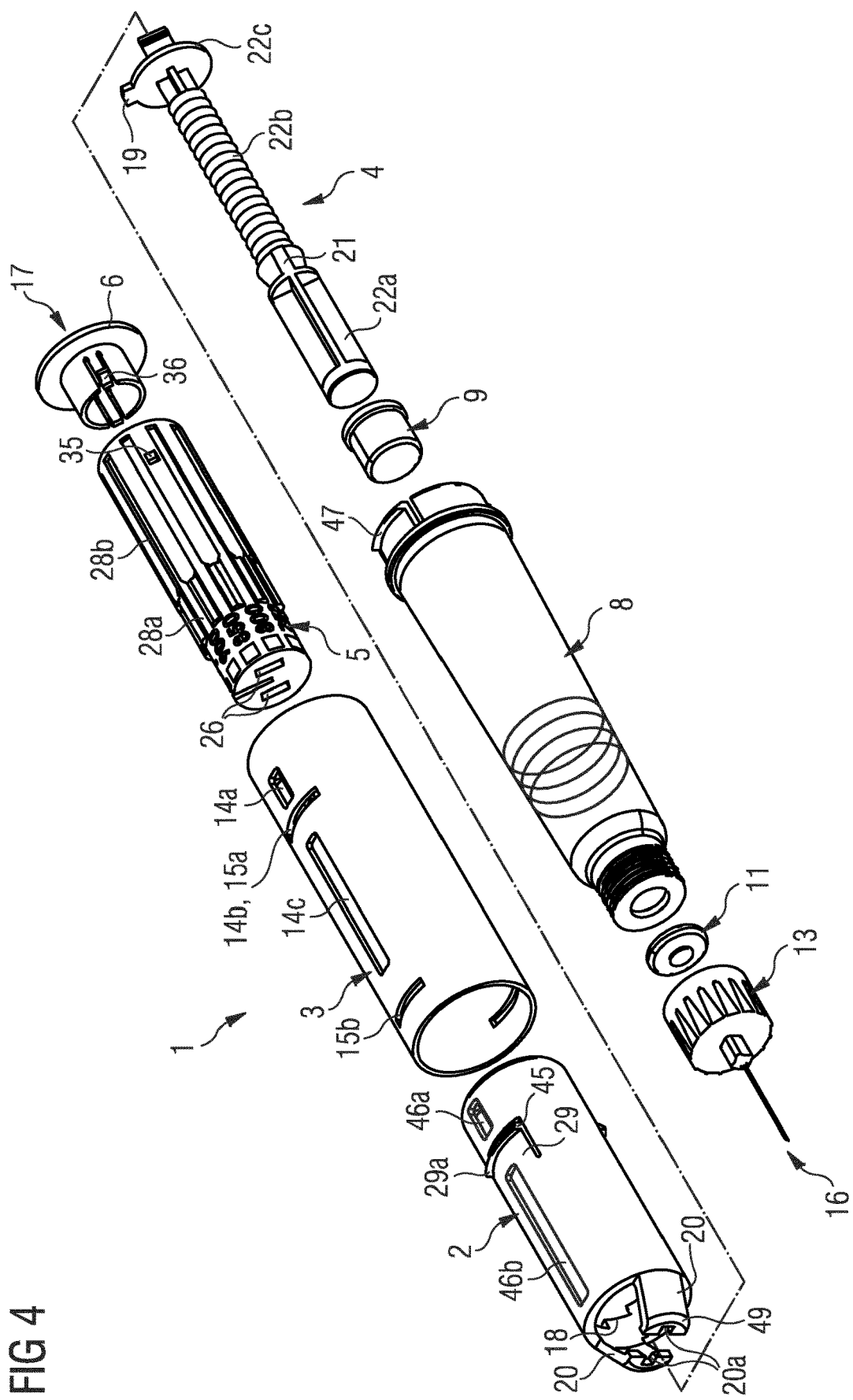

The end cap 6 is preferably non-releasably secured to the dose member 5. For example, the end cap 6 is snap-fitted to the dose member 5. For this purpose, the dose member 5 comprises fixing elements 35 (FIGS. 4 and 11, for example). The fixing elements 35 are arranged in a proximal end section of the dose member 5. The fixing elements 35 comprise two oppositely arranged cut-outs.

The end cap 6 comprises mating fixing elements 36 (FIG. 4). The mating fixing elements 36 are arranged in the distal section of the end cap 6. The mating fixing elements 36 comprise two hooks oppositely arranged on an outer surface of the side wall of the distal section. The hooks are resilient, in particular radially deflectable. In an alternative embodiment, the mating fixing elements 36 comprise two oppositely arranged deflectable tongues. The respective tongue may extend in the axial direction. The respective tongue may be delimited by two axial cut-outs in the surface of the end cap, in particular in the side wall of the distal section.

The fixing elements 35, 36 engage for non-releasably connecting the dose member 5 and the end cap 6 to one another. More precisely, end portions of the hooks/tongues are inserted into the cut-outs, thus protruding from the cut-outs and out of an outer surface of the dose member 5 for connecting the dose member 5 and the end cap 6. In this way, relative axial and rotational movement of the dose member 5 and the end cap 6 is prevented.

In an alternative embodiment (not explicitly shown), the end cap 6 may be glued to the dose member 5, for example. In a further alternative embodiment (not explicitly shown), end cap 6 and dose member 5 may be formed integrally, i.e. they may constitute a single component. In these embodiments, the fixing elements 35, 36 may be redundant.

The dose member 5 is configured for providing information about an operational state or condition of the device 1. Furthermore, the dose member 5 is configured for providing information about a set size of the dose of medication 10. For this purpose, symbols 38 are provided, e.g. molded, printed or glued, on the outer surface of the dose member 5. The symbols 38 are arranged circumferentially around the outer surface. The symbols 38 are arranged in the distal end section of the dose member 5. In particular, in this embodiment, two circumferentially arranged rows of symbols 38 arranged adjacently to one another are provided in the distal end section. Of course, further arrangements of symbols 38 are possible, e.g. three rows or only one row of symbols 38.

The symbols 38 comprise numerals relating to the size of the set dose. Moreover, the symbols 38 comprise a lock-symbol which is intended to indicate that the device 1 is in an unprimed state. In that state, the device 1 may not yet be ready for use, i.e. it is locked such that a dose setting operation is prevented. Furthermore, the symbols 38 comprise letters, in particular the letter "P" for indicating that the device 1 is in a primed ("P") state, i.e. it is no longer locked and, thus, ready for use. The symbols 38 may comprise color, e.g., a first color which may indicate that the device 1 is in a kind of intermediate state, e.g. a state where a dose has not yet been set correctly. The symbols 38 may also comprise a second color, for example red, for indicating a kind of "ready-state", e.g. that the dose was correctly set and that the device 1 is ready for dispensing the set dose. Further, the symbols 38 may comprise arrows which indicate the direction that the user must rotate or push the dose member 5 in order to perform the next use step (e.g. an axial arrow to indicate the need to prime the device 1, changing to a circumferential arrow to indicate the initial direction of rotation required to set a dose). Of course, different symbols, colors and/or letters are conceivable.

The symbols 38 are visible for the user through window apertures 14a, 14b, 14c (see FIGS. 1, 2 and 4). In particular, the body 3 comprises a first window aperture 14a, a second window aperture 14b and a third window aperture 14c. The first window aperture 14a is arranged in a proximal end section of the body 3. The first window aperture 14a is arranged more proximal than the second window aperture 14b and the third window aperture 14c. The second window aperture 14b is axially arranged between the first window aperture 14a and the third window aperture 14c.

The first and the third window aperture 14a, 14c extend along the longitudinal axis 23. The first window aperture 14a is smaller than the third window aperture 14c. In particular, the third window aperture 14c is longer, i.e. it comprises a greater extension along the longitudinal axis 23, than the first window aperture 14a. The axial extension of the third window aperture 14c is correlated with the maximum size of the dose to be set and dispensed from the device 1.

The second window aperture 14b extends perpendicular to the longitudinal axis 23. The reason for that is, that the second window aperture 14b has a further function in addition to the display of symbols 38. In particular, the second window aperture 14b acts as a connection or coupling element 15a for connecting a further component, e.g. the previously mentioned interaction member 2, to the body 3, which is described later on in detail.

The first window aperture 14a is adapted and arranged to display symbols 38 only in the unprimed state and during the dose setting operation. No symbols 38 will be displayed during dose delivery and in a locked condition of the device 1 after dose delivery was completed. In particular, the first window aperture 14a displays the lock-symbol in the unprimed state of the device 1. Moreover, once the device 1 is primed, the first window aperture 14a displays the P-symbol for indicating that the device 1 is now ready for use. During dose setting, the first window aperture 14a further displays the numerals for indicating the size of the dose which is set by the user.

Regarding the second window aperture 14b, this window aperture is adapted and arranged to display symbols 38 only when the device 1 is primed and, in particular, during the dose setting operation. No symbols 38 will be displayed in the unprimed state and during or after dose delivery. During dose setting, the second window aperture 14b displays the previously mentioned colors.

The third window aperture 14c displays information only at the end of the dose delivery operation. When the set dose was delivered, the size of the delivered dose as well as a color symbol are displayed in the third window aperture 14c. Accordingly, the third window aperture 14c is adapted and arranged to display symbols 28 belonging to both rows of symbols 38.

The dose member 5 further comprises a plurality of tracks 27 as can be gathered from FIG. 11, for example. The tracks 27 are adapted and arranged to mechanically cooperate with deflectable features 42, in particular deflectable detents 43, of the body 3 (see FIG. 12). The tracks are arranged between/are formed by means of ribs extending along the outer surface of the dose member 5.

The respective track 27 extends along the outer surface of the dose member 5. In the direction from the distal end towards the proximal end of the dose member 5, the tracks 27 are arranged after the symbols 38 and extend up to the proximal end section of the dose member 5. An azimuthal or rotational position of the respective track 27 with respect to the body 3 is correlated with the size of the set dose. In other words, each track 27 corresponds to one specific dose size. One numeral indicating the size of the set dose is assigned to one specific track 27.

The respective track 27 comprises different sections 28a, 28b. In particular, each track 27 comprises a first section 28a and a second section 28b. As seen from the distal end towards the proximal end, the first section 28a passes over into the second section 28b. The respective track 27, in particular its second section 28b, comprises a proximal end. Said proximal end is edged or limited by a wall 40. The respective track 27, in particular its first section 28a, comprises a distal end. The distal end is open. The distal end passes over directly to the numeral assigned to the respective track 27.

In azimuthal direction, the tracks 27 are enclosed or edged by first side walls 41a belonging to the first section 28a and second side walls 41b belonging to the second section 28b. In other words, the first section 28a is delimited in azimuthal direction by two first side walls 41a. The second section 28b is delimited in azimuthal direction by two second side walls 41b. The side walls 41, 41b constitute side faces of the previously mentioned ribs.

The first section 28a and the second section 28b are differently shaped. The first section may be broader than the second section 28b. In other words, an extension of the first section 28a in azimuthal direction may be greater than the extension in azimuthal direction of the second section 28b. For example, the first section 28a may be 1.5 times broader than the second section 28b. In an alternative embodiment, the first section 28a and the second section 28b may have the same breadth. Alternatively, the second section 28b may be broader than the first section 28a.

A transition region between the first section 28a and the second section 28b extends oblique to the longitudinal axis 23 for guiding the previously mentioned deflectable feature 42 from the first section 28a into the second section 28b.

Moreover, the side walls 41b of the second section 28b are steeper than the side walls 41a of the first section 28a. The side walls 41b of the second section 28b extend preferably perpendicular to the longitudinal axis 23. The corresponding ribs and, thus, the side walls 41b of the respective second section 28b are edged.

The ribs and, thus, the side walls 41a of the respective first section 28b are rounded. If it is desirable to make the rotation one-way only, this might be accomplished by asymmetric forms of side walls 41a. In such an embodiment, that side wall 41a of the respective first section 28a which is arranged in the rotational direction of the dose member 5 (e.g. the right side wall 41a of a respective track 27 in FIG. 11) may be more rounded than that side wall 41a which is arranged in the opposite rotational direction (e.g. the left side wall 41a of a respective track 27 in FIG. 11). In this way, the dose member 5 may be prevented from being rotated in a direction which is opposite from the rotational direction.

However, it seems to be preferable to generally permit both upwards and downwards selection of doses—with the following exception: In particular, it is advantageous to prevent the user from dialling direct from "P" to "900" (i.e. the maximum dose) in the direction opposite to the previously mentioned rotational direction. Instead, the user must dial/rotate in the rotational direction all the way up to "900" in the rotational direction (via "500" etc.). This makes dialling an accidental overdose less likely. This exception is achieved by a specific shape (less rounded shape) of the corresponding side wall 41a separating/lying between "P" and "900", as described above.

Moreover, the rib delimiting the respective second section 28b is higher. In other words, the second section 28b is deeper than the first section 28a. The respective second side wall 41b is higher than the respective first side wall 41a.

The specific shape and structure of the first section 28a makes this section overridable by the deflectable feature 42 such that the dose member 5 can be rotated when the deflectable feature 42 mechanically cooperates with the first section 28a. The specific shape and structure of the second section 28b makes this section non-overridable by the deflectable feature 42 such that the dose member 5 cannot be rotated when the deflectable feature 42 mechanically cooperates with the second section 28b. The differently shaped sections 28a, 28b of the tracks 27 thus enable the setting of discrete doses (first section 28a) by rotation of the dose member 5. The differently shaped sections 28a, 28b of the tracks 27 further enable a rotational lock and an axial guidance of the dose member 5 (second section 28b) during dose delivery.

Figure 12:
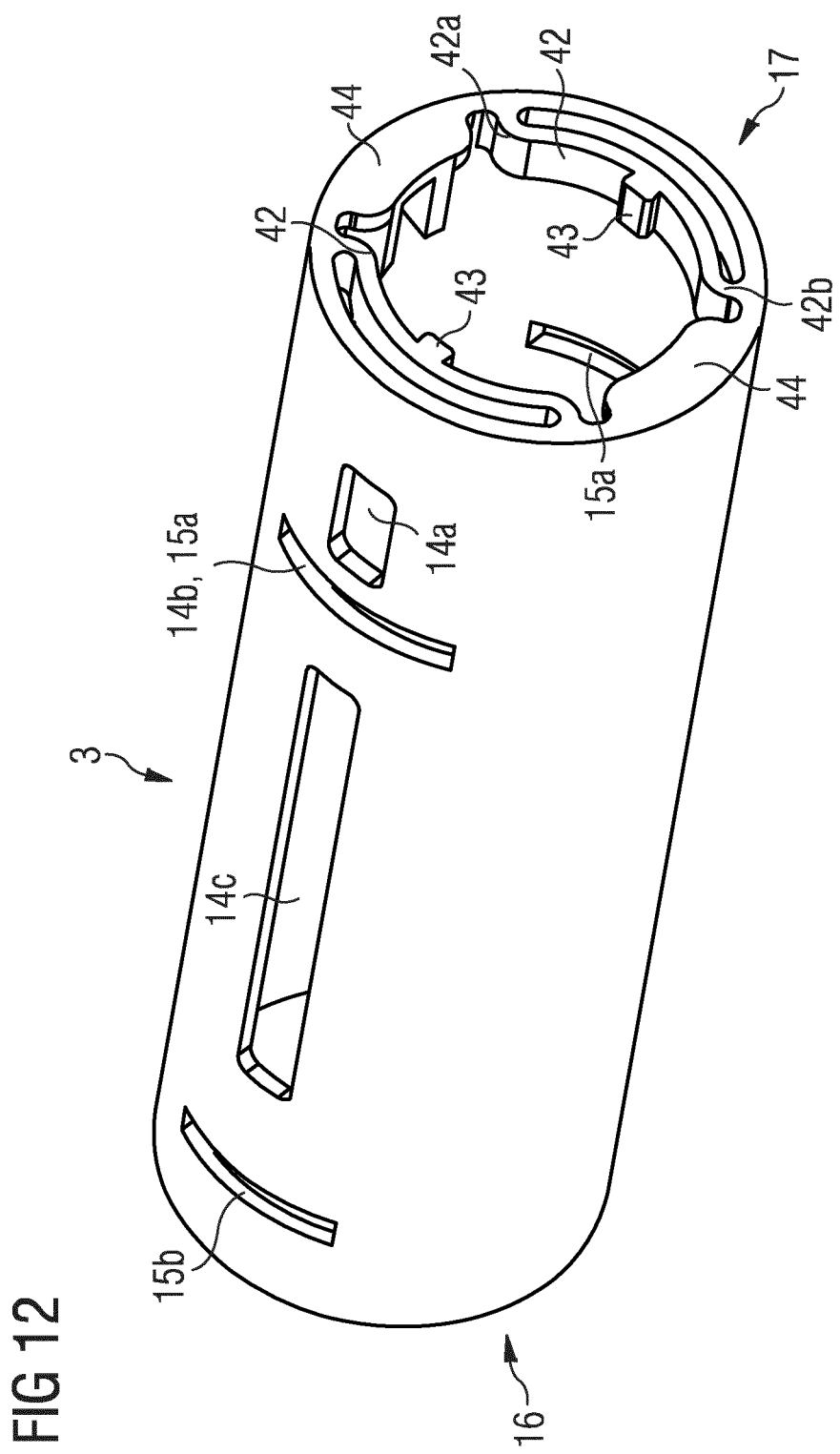

For enabling the above mentioned functions, the body 3 comprises the previously mentioned deflectable features 42, which are depicted in FIG. 12. The body 12 comprises two oppositely arranged deflectable features 42. Of course, different numbers of deflectable features 42, e.g. one or three deflectable features 42, are possible. The deflectable features 42 are arranged on the proximal end of the body 3. The body 3 comprises an open proximal end. The deflectable features 42 protrude from an inner surface of the body 3 in the radial direction and into the open proximal end of the body 3.

The respective deflectable feature 42 is deflectable in the radial direction. The respective deflectable feature 42 comprises a spring arm. The respective deflectable feature 42 comprises a first end section 42a and a second end section 42b. Both end sections 42a, 42b emerge from the inner surface of the body 3. In other words, the deflectable feature 42 comprises no free end section 42a, 42b. Rather, the end sections 42a, 42b pass over into the inner surface. In this context, it should be noted that the deflectable feature 42 and the body 3 are integrally formed.

The respective deflectable feature 42 comprises a detent 43. The detent 43 protrudes from the deflectable feature 42 in the radial inward direction towards a central region of the open proximal end of the body 3. The detents 43 are symmetrically arranged. The respective detent 43 is—together with the deflectable feature 42—deflectable in the radial direction.

The respective detent 43 is adapted and arranged to mechanically cooperate with the first and second sections 28a, 28b of the tracks 27. In other words, the respective detent 43 comprises a position with regard to the respective track 27 as well as an outer shape, which enable the detent 43 to engage, preferably releasably engage, with the first section 28a of a respective track 27. Moreover, the respective detent 43 comprises a position with regard to the respective track 27 as well as an outer shape, which enable the detent 43 to engage, preferably non-releasably engage, with the second section 28b of a respective track 27. The detent 43 may be rectangularly shaped. Of course, other shapes, which enable the detent 43 to engage the tracks 27, are possible. The respective detent 43 may have rounded edges to prevent jamming of the detent 43 with the tracks 27.

The respective detent 43 has an azimuthal extension which must not exceed the azimuthal extension of the second section 28b of a respective track 27. In particular, the azimuthal extension of the respective detent 43 should be at least marginally smaller than the azimuthal extension of the second section 28b of a respective track 27.

During the dose setting operation, the dose member 5 is rotated. Thereby, the respective detent 43 mechanically cooperates with the first section 28a. In particular, the dose member 5 comprising the tracks 27 is rotated, the first sections 28a thereby being rotated over the detent 43. The detent 43 slides from the first section 28a of one respective track 27 over the rounded side wall 41a and into the first section 28a of the adjacent track 27 and so on. In other words, it overrides the first section 28a and, thus, the rounded rib delimiting the first section. At the end of the dose setting operation, the detent 43 is positioned in the first section 28a of a specific track 27 the rotational/azimuthal position of which is correlated with the size of the set dose.

For dose delivery, the dose member 5 is moved in the distal direction. Thereby, the specific track 27 slides along the detent 43. Upon distal movement of the dose member 5, the detent 43 passes over into the second section 28b of the specific track 27 guided by the oblique side wall of the transition area between the first section 28a and the second section 28b. When the detent 43 mechanically cooperates with the second section 28b, further rotation of the dose member 5 for setting a further dose of the medication 10 is prevented due to the specific shape of the second section 28b. In particular, the detent 43 cannot override the high and steep side walls 41b of the second region 28b/the edged ribs delimiting the second region 28b which would be necessary for the dose member 5 to be rotated.

Accordingly, once the dose has been set and the dose delivery operation has begun, the detent 43 remains in the specific track 27. Movement of the dose member 5 during dose delivery is axially guided due to the second section 28b mechanically cooperating with the detent 43. A modification of the size of the set dose (by counter-rotation) as well as setting of a further dose (by rotation in the rotational direction) is prevented. Hence, the detent 43 and the second section 28b constitute a lock-out feature for the device 1.

The body 3 finally comprises two symmetrically arranged protrusions 44 (see FIG. 12). The protrusions 44 are arranged between the deflectable features 42, respectively. The protrusions 44 comprise rounded edges. The protrusions 44 mechanically stabilize the body 3. Moreover, the protrusions 44 are arranged to linearly guide the dose member 5 when the dose member 5 is at least partly inserted into the body 3 during assembly of the device 1. While the detents 43 are arranged to protrude towards the level of the troughs/ tracks of the second sections 28b, the protrusions 44 are arranged to protrude to the level of the peaks of the second sections 28b.

Figure 9:
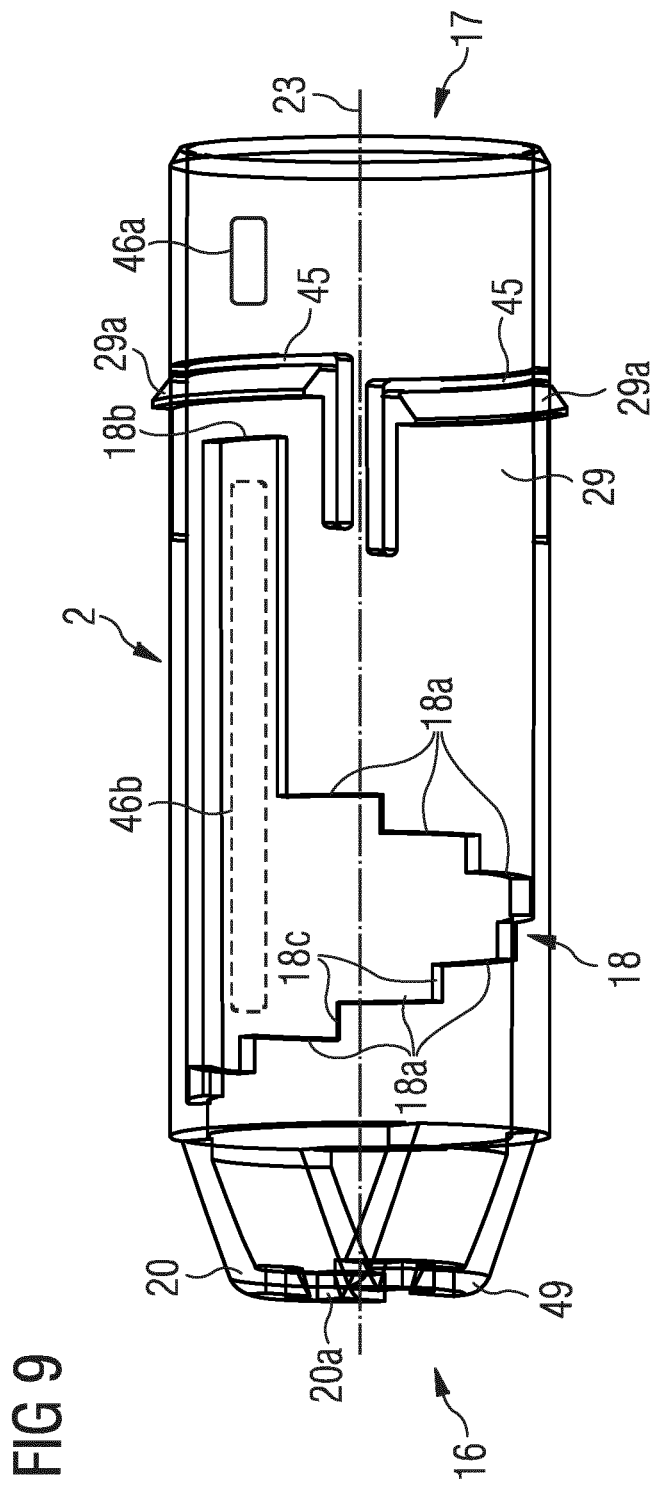

The device 1 further comprises the previously mentioned interaction member 2 (see, for example, FIGS. 1 and 9). The interaction member 2 is shaped tubular-like. The interaction member 2 may be an interaction sleeve. The interaction member 2 is arranged completely within an interior of the body 3. The interaction member 2 may be an inner sleeve of the body 3. The interaction member 2 is secured against axial and rotational movement with respect to the body 3. In particular, the body 3 and the interaction member are coupled, in particular non-releasably coupled, to another such that relative movement between the body 3 and the interaction member 2 is prevented. For example, the interaction member 2 and the body 3 may be snap-fitted to one another. Alternative embodiments are possible, e.g. the interaction member 2 and the body 3 may be glued to one another.

The body 3 and the interaction member 2 comprise coupling elements 15a, 29. The body 3 comprises two oppositely arranged coupling elements 15a. The coupling elements 15a are provided as apertures which extend perpendicular to the longitudinal axis 23 (see FIGS. 1, 2 and 12, for example). One of the said coupling elements 15a/ apertures is further adapted and arranged to display information to the user, i.e. it constitutes the previously described second window aperture 14b. Accordingly, at least one of the said apertures provided in the body 3 is a multifunctional aperture.

The interaction member 2 comprises two oppositely arranged mating coupling elements 29 (see, for example, FIG. 9). The mating coupling elements 29 are arranged in a proximal section of the interaction member 2. The mating coupling elements 29 comprise resilient tongues. However, alternative embodiments for the mating coupling elements 29 are possible, e.g. a hook/or a rib. The resilient tongues are radially deflectable. The respective resilient tongue is realized by providing a U-shaped cut-out 45 of the interaction member 2. Thereby, a horizontal stroke or bar of the "U" extends perpendicular to the longitudinal axis 23. The two vertical strokes or bars of the "U" extend along the longitudinal axis 23. The respective tongue extends between the two vertical strokes or bars of the "U in the proximal direction towards the horizontal stroke of the "U". A tip of the respective mating coupling element 29/tongue comprises a protrusion 29a. The protrusion 29a extends along the whole tip of the coupling element 29. The protrusion 29a extends perpendicular to the longitudinal axis 23.

The protrusion 29a extends from the tip of the respective coupling element 29 in the radial outward direction. The protrusion 29a is oblique. This means that the protrusion 29a comprises a side wall, in this embodiment a proximal wall, which is oblique to an axis perpendicular to the longitudinal axis 23. The protrusion 29a engages the coupling element 15a when the interaction member 2 is connected to the body 3.

For coupling the interaction member 2 and the body 3 to one another, the interaction member 3 is introduced into the body 3, e.g. from its open distal end, and is moved in the proximal direction within the body 3. Thereby, the respective mating coupling element 29 and, in particular, the protrusion 29a is deflected in the radial inward direction due to mechanical cooperation with the inner surface of the body 3. Once the protrusion 29a and the coupling element 15a overlap, the protrusion 29a deflects in the radial outward direction through the coupling element 15a and out of the body 3 (see, for example, FIGS. 1 and 5) for non-releasably coupling the interaction member 2 and the body 3. When the interaction member 2 and the body 3 are connected, the horizontal stroke of the cut-out 45 overlaps with the second window aperture 14b of the body 3 for displaying the symbols 38 described above.

The interaction member 2 comprises further window apertures 46a, 46b, in particular a first window aperture 46a and a second window aperture 46b as can be gathered from FIG. 4. The first window aperture 46a is arranged in the proximal end section of the interaction member 2 and extends in the longitudinal direction. The second window aperture 46b is arranged more distal than the first window aperture 26a and extends in the longitudinal direction, too. As seen in the axial direction the cut-out 45 is arranged between the first window aperture 46a and the second window aperture 46b.

When the interaction member 2 and the body 3 are connected, the first window aperture 46a overlaps with the first window aperture 14a of the body 3 (see FIG. 1). Moreover, the second window aperture 46b overlaps with the third window aperture 14c of the body 3. A shape, axial extension and/or azimuthal extension of the first window aperture 46a corresponds to the shape, axial extension and/or azimuthal extension of the first window aperture 14a of the body 3. A shape, axial extension and/or azimuthal extension of the second window aperture 46b corresponds to the shape, axial extension and/or azimuthal extension of the third window aperture 14c of the body 3.

The interaction member 2 further comprises two oppositely arranged pawl means 20, e.g. pawl arms. The pawl means 20 are arranged in the distal end section of the interaction member 2. The pawl means 20 emerge from the interaction member 2 and are, in particular, integrally formed with the interaction member 2.

The pawl means 20 are radially deflectable. The respective pawl means 20 comprises a proximal end. The respective pawl means 20 comprises a distal end or tip 49. The distal end 49 is a free end. The distal end 49 of the respective pawl means 20 is broadened in the radial direction. In particular, the distal end 49 extends in the radial inward direction. The respective pawl means 20 is oblique with respect to the longitudinal axis 23. A radial distance between the two pawl means 20 at the distal end 49 is smaller than the radial distance between the two pawl means 20 at the proximal end. The radial distance between the tips 49 of the two pawl means 20 in a relaxed/unbent state is smaller than a diameter of the piston rod 4. The distal end of tip 49 constitutes an engagement feature of the respective pawl means 20 adapted and arranged for mechanical interaction with the piston rod 4.

The pawl means 20 are adapted and arranged to mechanically cooperate with the piston rod 4, in particular with its first axial region 22a, when the device 1 is in the unprimed state. The respective pawl means 20, in particular its distal end or tip 49, comprises a recess 20a. Accordingly, the distal end or tip 49 is shaped like a half ring. In the unprimed state, the respective recess 20a mechanically cooperates with the previously described anti-rotation feature 21 for preventing rotation of the piston rod 4 in the unprimed state. In other words, in the unprimed state, the interaction member 2 and the piston rod 4 are splined to one another. Moreover, the distal end or tip 49 of the pawl means 20 abuts a proximal surface of the previously described plate-like structure 31 which is part of the first axial region 22a of the piston rod 4. Proximal movement of the piston rod 4 in the unprimed state is, thus, prevented.

During the priming operation, the piston rod 4 is moved slightly distally and the pawl means 20 is brought out of engagement with the anti-rotation feature 21. Accordingly, after the device 1 was primed, rotation of the piston rod 4 in the rotational direction is enabled. When the piston rod 4 is rotated during dose setting, the pawl means 20 slide over the structured surface of the second axial region 22b of the piston rod 4. In particular, the pawl means 20 is slid around the distal edge 24b of the most distal ratchet tooth 24/cone-shaped segment arranged on the piston rod 4.

The interaction member 2 further comprises a stop member 18 (see, in particular, FIGS. 4 and 9). The stop member 18 is adapted and arranged to mechanically cooperate with the piston rod 4, in particular with the contact element 19 of the piston rod 4. In specific operational states of the device 1, which states are described later on in detail, the contact element 19 abuts the stop member 18, in particular parts of the stop member 18.

The stop member 18 is wound around an inner surface of the interaction member 2. The stop member 18 is according the depicted embodiment helically arranged around the inner surface of the interaction member 2. However, if steps between different doses are not equal, then the stop member 18 is not helical as described above. The stop member 18 extends at least along half of the axial extension of the interaction member 2. The stop member 18 occupies a majority of the inner surface of the interaction member 2.

The stop member 18 may be regarded as a system of axially extending half-tracks or "track-fractions". In this context, the term "half-track" shall mean that at least a part of the side walls and/or a proximal wall usually delimiting an axial track may be missing. For example, the respective half-track may have no side walls or only one side wall or only the fraction of a side wall. However, the respective half-track may comprise a distal wall as explained in the following. It is emphasized herewith that the stop member 18 does not comprise conventional tracks comprising side walls used for an axial guidance of the piston rod 4. Axial guidance is provided by the tracks 27 (in particular the second section 28b of the tracks 27) of the dose member 5. The term "track" must, thus, not be misunderstood as a groove or indentation in which the piston rod 4 is guided.

The stop member 18 comprises a plurality of axial end stops 18a. The respective axial end stop 18a extends perpendicular to the longitudinal axis 23. The respective axial end stop 18a can be regarded as an end wall, i.e. the distal wall, delimiting a respective axial half-track on the inner surface of the interaction member 2. The respective axial end stop 18a has an azimuthal extension which is slightly greater than the azimuthal extension of the contact element 19 of the piston rod 4.

The respective axial end stop 18a has a specific axial position with respect to the inner surface of the interaction member 2 and/or with respect to the body 3. The axial position is correlated with the size of the dose set and dispensed from the device 1. The closer the respective axial end stop 18a is arranged to the dispensing end of the device 1, the greater the size of the set dose. The further away the respective axial end stop 18a is arranged from the dispensing end of the device 1, the smaller the size of the set dose.

The respective axial end stop 18a is configured to limit or determine a distance by which the piston rod 4 is displaced in the distal direction during dose delivery. When the piston rod 4 is rotated during dose setting, the piston rod 4, in particular its contact element 19, becomes axially aligned with a specific axial end stop 18a. As set forth above, the term "specific" means in this context, that said axial end stop 18a is correlated with the size of the set dose and, accordingly, with the rotational position of the piston rod 4 after the dose setting operation was completed. When delivering the set dose, the piston rod 4, in particular its contact element 19, is moved towards this specific axial end stop 18a. At the end of the dose delivery operation, the piston rod 4, in particular the contact element 19, abuts this specific axial end stop 18a such that further distal movement of the piston rod 4 is prevented.

The stop member 18 further comprises a plurality of rotational or azimuthal end stops 18c. The respective rotational end stop 18c extends along the longitudinal axis 23. Two adjacent axial end stops 18a are connected by a rotational end stop 18c. The respective rotational end stop 18c may be regarded as the vertical part of a step of a staircase whereas the respective axial end stop 18a may be regarded as horizontal part of the step of the staircase. Altogether, the axial and rotational end stops 18a, 18c constitute a, for example helical, staircase.

The respective rotational end stop 18c also has a specific axial position with respect to the inner surface of the interaction member 2 and/or with respect to the body 3. As it is the case for the respective axial end stop 18a, an axial position of the respective rotational end stop 18c is correlated with the size of the dose of medication 10. The respective rotational end stop 18c is configured to prevent further rotation of the piston rod 4 after the set dose has been dispensed from the device 1. In other words, the respective rotational end stop 18c constitutes a final lock-out feature of the device 1. This duplicates the previously described function of the second sections 28b/detents 43 on the dose setting member 5 and the body 3. Accordingly, there may be embodiments in which the rotational end stop 18c is redundant.

When the piston rod 4 is rotated during dose setting, the piston rod 4, in particular its contact element 19, becomes azimuthally aligned with a specific rotational stop 18c. Said specific rotational end stop 18c is directly adjacent to the axial end stop 18a the piston rod 4 becomes axially aligned with during dose setting. In this context, the term "azimuthally aligned" shall mean that a side wall 19a (see FIG. 10) of the contact element 19 comprises almost the same azimuthal position with respect to the inner surface of the interaction member 2 as the specific rotational end stop 18c. In particular, at the end of the dose setting operation, the specific rotational end stop 18c may be positioned marginally further towards the rotational direction as the contact element 19.

When delivering the set dose, the piston rod 4, in particular its contact element 19, is moved distally until it abuts the axial end stop 18a. When the contact element 19 abuts the specific axial end stop 18a, the contact element 19 has the same axial position as the specific rotational end stop 18c. Accordingly, at the end of the dose delivery operation, the specific rotational end stop 18c prevents further rotation of the piston rod 4 for setting a further dose of the medication 10. At the end of the dose delivery, the piston rod 4 can only be rotated marginally until it is brought into direct contact with the specific rotational end stop 18c. Mechanical cooperation of the specific rotational end stop 18c and the contact element 19 then prevents further rotation of the piston rod 4.

The stop member 18 further comprises an axial priming stop 18b. The axial priming stop 18b is arranged in a proximal end section of the interaction member 2. In particular, the axial priming stop 18b is arranged closer to the proximal end of the interaction member 2 than any one of the axial end stops 18a. The axial priming stop 18b extends perpendicular to the longitudinal axis 23. The axial priming stop 18b has an azimuthal extension which is slightly greater than the azimuthal extension of the contact element 19 of the piston rod 4.

This arrangement, i.e. the axial priming stop 18c and the axial end stops 18a all being located on the same component, ensures that the best possible dose accuracy is obtained. This is because each dose is controlled by a single dimension formed in a single component. I.e. there is no stack up of tolerances across several features/components controlling the travel of the piston rod 4.

Before the device 1 is primed, the piston rod 4 and, in particular, the contact element 19, is already axially aligned with the axial priming stop 18b. For priming the device 1, the piston rod 4 is moved distally. The piston rod 4 stops when the contact element 19 abuts the axial priming stop 18b. The axial priming stop 18b prevents further movement of the piston rod 4 in the distal direction. Before the piston rod 4 can further be moved distally, it must be rotated clear of the axial priming stop 18b. In other words, a dose setting operation must be performed.

In an alternative embodiment (not explicitly shown), the stop member 18 and the pawl means 20 may be part of the body 3. This means that the stop member 18, the pawl means 20 and the body 3 may constitute a single component of the device 1. In particular, the stop member 18 may be arranged around an inner surface of the body 3. The pawl means 20 may protrude from the distal end face of the body 3. In this embodiment, the previously described interaction member 2 may be superfluous.

In the following, operation of the medication delivery device 1 is described in detail in connection with FIGS. 5, 6, 7 and 8.

Figure 5:
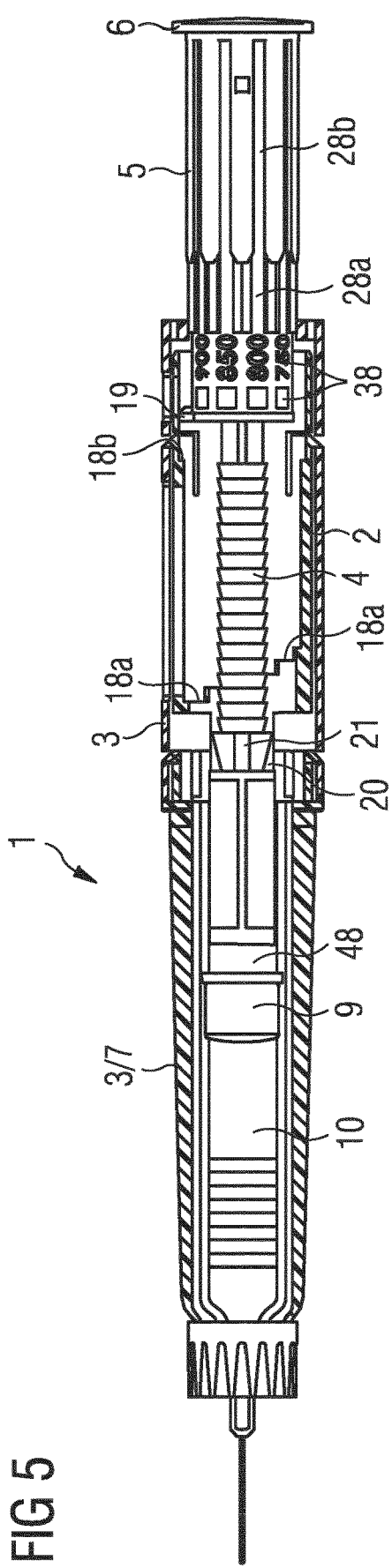

FIG. 5 shows the device 1 as supplied from the manufacturer. The device 1 contains the medication 10, in particular one dose of the medication 10. As described previously, the size of the dose is variable. Accordingly, the device 1 must contain sufficient medication for setting and dispensing a maximum settable dose from the device 1, e.g. 900 Units. For the case that less than the maximum settable dose, e.g. the minimum possible dose of the medication 10, is set and dispensed, medication 10 will be left over in the device 1. This remaining medication 10 will be discarded together with the device 1 after delivery of the set dose of the medication 10.

When the device 1 is supplied to the user, the device 1 is in the unprimed state or condition. In this case, the lock-symbol 38 (see FIG. 11) is visible in the first window aperture 14a of the body 3. The further window apertures 14b, 14c do not show any symbols 38 in this state of the device 1.

In the unprimed state, there may be air in the section of the body 3/in the cartridge 8 containing the medication 10. In the unprimed state, there may be a gap 48 between the piston rod 4 and the dose 9. The gap 48 may arise from manufacturing and/or assembly tolerances of components of the device 1. The size of the gap 48 may vary. However, in the delivery condition, i.e. when delivering the set dose of the medication 10, a gap 48 between the piston rod 4 and the dose 9 respectively air in the device 1 may affect the dose accuracy, in particular for a variable dose device as described herein. More precisely, what makes dose accuracy of the variable dose device 1 so significant is that it is much more difficult to be accurate compared to a device delivering the entire contents. This is because the device must perform the metering function—it cannot rely on the fill volume being accurate and then simply pushing out all of the medication. Hence, the elimination of the gap 48 and/or air become crucial in order to obtain the dose accuracy required.

For that reason, the device 1 may not be operated unless a priming operation was performed by the user. In particular, in the unprimed state, a dose setting operation is prevented as the pawl means 20 of the interaction member 2 (only indicated in FIG. 5, see in particular FIGS. 4 and 9) engage the anti-rotation feature 21 of the piston rod 4, thus preventing the piston rod 4 (and accordingly the dose member 5) from being rotated in the rotational direction for setting the dose of the medication 10.

For priming the device 1 and, thus, for bringing the device 1 in a condition ready for setting and dispensing the dose of the medication 10, the user presses onto the end cap 6. Accordingly, the dose member 5 is moved in the distal direction. The piston rod 4 is moved distally along with the dose member 5 as these components are rotationally and axially coupled to one another as described above.

Figure 6:
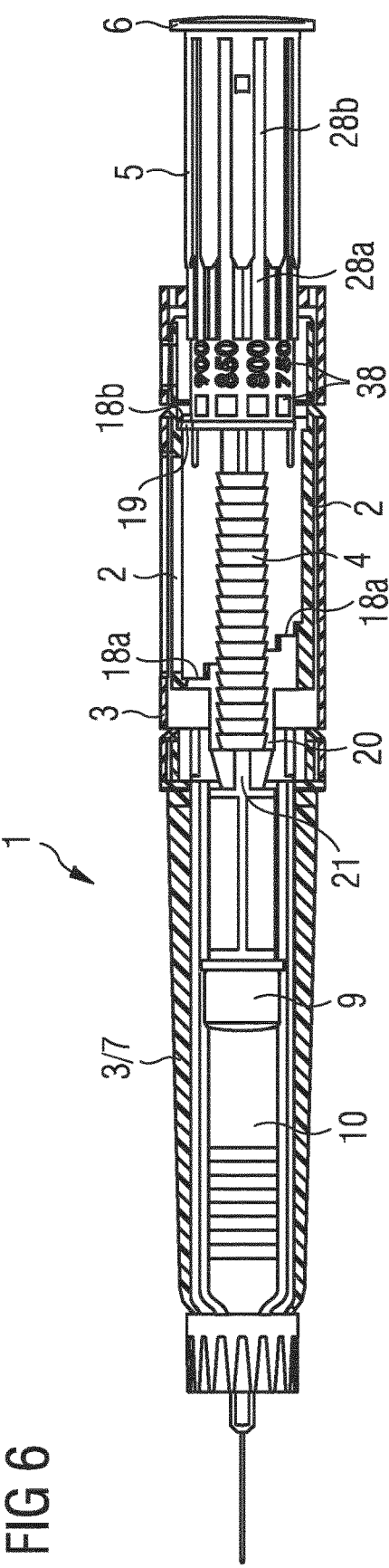

When the piston rod 4 is moved in the distal direction during the priming operation the gap 48 between the dose 9 and the piston rod 4 is closed (see FIG. 6 which depicts the condition of the device 1 after having performed the priming operation). When the piston rod 4 is moved in the distal direction during the priming operation, air and/or medication 10 will be expelled from the device 1 through the needle 12. In particular, air will only be expelled if the device 1 is being held "needle-end-upwards" at the time. However, even if the air is not expelled (i.e. if it remains in the device 1 after priming) the dose accuracy of the device 1 will still be significantly improved versus an unprimed device because of the elimination of the gap 48.

When the piston rod 4 is moved distally during priming, the contact element 19 is moved towards the axial priming stop 18b of the interaction member 2 (see also FIGS. 9 and 10). After a certain distance, for example 4 mm, of distal travel, the contact element 19 abuts the axial priming stop 18b. Accordingly, the axial priming stop 18b limits distal travel of the piston rod 4 during priming. When the contact element 19 abuts the axial priming stop 18b, the priming operation has been finished. The gap 48 has been removed.

When the piston rod 4 is moved in the distal direction during the priming operation, the anti-rotation feature 21 slides out of engagement with the recess 20a of the pawl means 20 (see FIG. 4). In particular, when the contact element 19 abuts the axial priming stop 18b, there is no longer mechanical contact between the recess 20a and the anti-rotation feature 21. Rather, the two pawl means 20 now mechanically cooperate with the second axial region 22b of the piston rod 4.

When the pawl means 20 pass over from the first axial region 22a into the second axial region 22b of the piston rod 4, the pawl means 20 slide over the cone shaped proximal end section of the first axial region 22a, thereby being deflected radially outwardly. In the embodiment shown, the maximum diameter of the cone shaped proximal end section of first axial section 22a (the priming section of the piston rod 4) is significantly larger than the maximum diameter of the cone-shaped segments in the second axial region 22b. However, in an alternative embodiment, the plate-like structure 32 may have the same maximum diameter as the ratchet teeth 24, in particular their proximal etches 24a. In this way, deflection of the pawls means 20 and, thus, the injection force during the priming stroke may be reduced. Furthermore, weakening of the pawls means 20 (by plastic deformation) may be avoided or at least reduced.

When the pawl means 20 have passed the plate-like structure 32, the pawl means 20 relax in the radial inward direction such that the pawl means 20 abut the second axial region 22b. The pawl means 20 are now arranged in the distal end section of the second axial region 22b close to the plate-like structure 32. The piston rod 4 is rotatable and the device 1 is ready for setting the dose of the medication 10. This condition is depicted in FIG. 6.

When the device 1 has been primed, the "P"-symbol is visible through the first window aperture 14a. Further, at the end of the priming operation, the second window aperture 14b displays a color, e.g. a green color for indicating that the device 1 is in the operational mode or, alternatively, a red color for indicating that a dose has not yet been set. The third window aperture 14c does not show any symbols 38 in this state of the device 1. Rather, an outer surface of the piston rod 4 may be visible through said window aperture 14c.

In FIG. 6, the piston rod 4 is arranged more distal than it is the case for the device 1 shown in FIG. 5. The device 1 is primed. Now, the user can set the desired dose of the medication 10. For that purpose, the user grips the dose member 5 and rotates it in the rotational direction, e.g. the anti-clockwise direction. Rotation in the opposite direction may be prevented due to the specific shape of the side walls 41a of the first section 28a of the tracks 27. As mentioned previously, that side wall 41a of the first section 28a of a respective track 27, which is arranged closer to the rotational direction than the other side wall 41a can be more rounded and it can be less steep so that the detent 43 can pass over the side wall 41a which is arranged closer to the rotational direction but it may not pass over the other/opposite side wall 41a for rotating the dose member 5 in the opposite direction.

However, alternative embodiments may include equally shaped first side walls 41a such that a counter rotation of the dose member 5 and, thus, a correction of the set dose may be possible. More precisely, as described above, it may be advantageous to allow the user to correct the dose but to prevent rotation back of the dose member 5 to the priming section or to prevent initial dialling from priming to the maximum dose.

When the dose member 5 is rotated, the tracks 27 are slid over the respective deflectable detent 43. In particular, upon rotation of the dose member 5, the detent 43 "moves" (in fact, the detent 43 is not moved but the tracks 27 are moved) from the first section 28a of a respective track 27 into the first section 28a of that track 27 which succeeds the first track 27 in the rotational direction. Thereby, the detent 43 is slid over the rounded side wall 41a of the respective first section 28a/the rounded rib delimiting the first section 28a. When the detent 43 passes over the side wall 41a/the rib, the detent 43 is deflected radially outwardly. When the detent 43 engages the adjacent track 27, it relaxes in the radially inward direction.

The detent 43 controls the rotational position of the dose member 5. In this way, only discrete doses of the medication 10 can be set. In particular, the dose is set correctly only when the detent 43 is positioned in or engages with the first section 28a of a respective track 27. As the detent is radially deflectable, the detent 43 has the tendency to rotatably shift the dose member 5 in the rotational direction by sliding over the rounded side wall 41a until the detent 43 is positioned in the adjacent track 27 corresponding to a specific dose size.

The piston rod 4 is rotated along with the dose member 5 in the rotational direction. Thereby, the pawl means 20 mechanically cooperate with the second axial region 22b of the piston rod 4. The protruding tip 49 of the pawl means 20 is arranged between the plate-like structure 32 and the proximal edge 24a of the most distal ratchet tooth 24 of the second axial region 22 so that the piston rod 4 can be rotated with respect to the pawl means 20. Thereby, the tip 49 of the pawl means 20 slides around the outer surface of the piston rod 4, in particular around the distal edge 24b of the most distal ratchet tooth 24/segment.

Upon rotation of the piston rod 4, the contact element 19 slides clear of the axial priming stop 18b. In particular, due to the rotation, the contact element 19 is moved into an azimuthal position different from the azimuthal position of the axial priming stop 18b with respect to the body 3. Due to the rotation, the contact element 19 becomes axially aligned with an axial end stop 18a. Which axial end stop 18a is finally aligned with the contact element 19 depends from the size of the dose finally set by the user.

When the dose member 5 and the piston rod 4 are rotated, a numeral indicating the size of the dose becomes visible through the first window aperture 14a dependent from the rotational position of the dose member 5 with respect to the body 3. The second window aperture 14b displays color. When the detent 43 just passes over from one track 27 into the adjacent track 27, a different color may be displayed as for the case when the detent 43 is positioned within the first section 28a of the respective track 27. For example, when the detent 43 passes from one track to another, green color may be displayed to indicate that no dose has been set so far. When the detent 43 is positioned within the first section 28a, red color may be displayed to indicate that a certain dose is chosen. Of course, other colors and another allocation of the colors to the state of the device 1 may be chosen.

The dose member 5 and, hence, the piston rod 4, is rotated until the desired size of the dose has been set. When the desired dose size is set, e.g. the maximum possible size of the dose, for example 900 Units, the detent 43 is positioned in the first section 28a of that specific track 27 correlating with the size of the set dose. The contact element 19 of the piston rod 4 is axially aligned with the corresponding axial stop element 18a. In the case that the maximum settable dose was chosen, this axial stop element 18a is the most distal stop element. The size of the set dose is displayed through the first window aperture 14a. A specific color is displayed by the second window aperture 14b.

Figure 7:
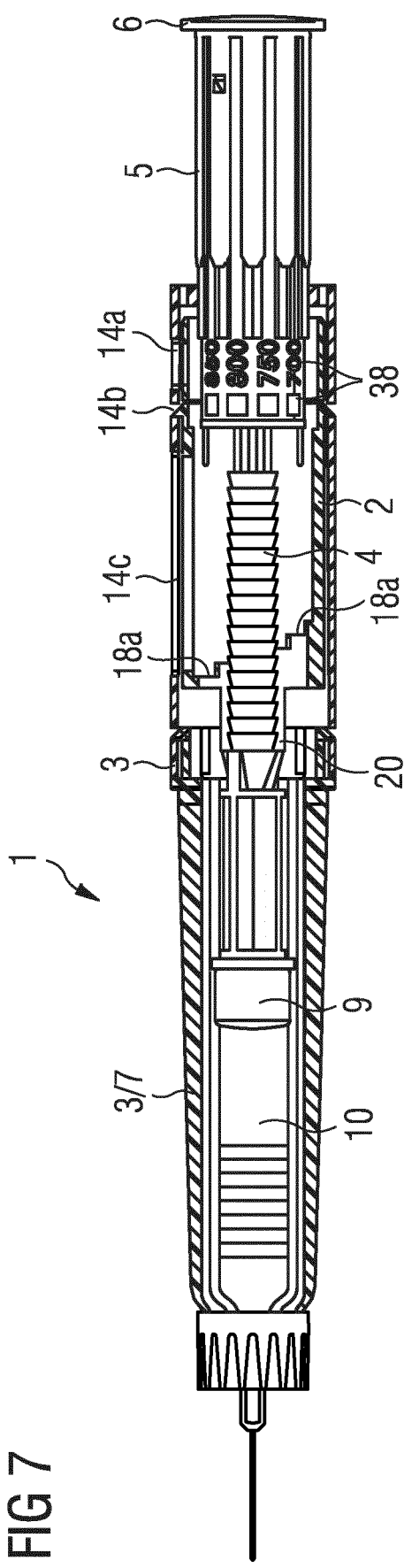

Now, the device 1 is ready for delivery of the set dose of the medication 10. This situation is depicted in FIG. 7. For delivering the set dose, the user pushes onto the end cap 6. The dose member 5 and, thus, the piston rod 4 are moved in the distal direction. When the piston rod 4 is moved distally, the pawl means 20 is slid along the straight ratchet teeth 24/segments of the piston rod 4, thereby creating an audible feedback to the user that the set dose is being dispensed. In particular, when the pawl means 20 passes along the distal (oblique) edge 24*b* of the respective ratchet tooth 24/segment, the pawl means 20 is deflected in the radial outward direction. A maximum deflection of the pawl means 20 is reached when it is arranged in a transition area between the proximal edge 24*a* and the distal edge 24*b*. After having passed the proximal edge 24*b* of the ratchet tooth 24, the pawl means 20 relaxes for engaging the distal edge 24*b* of the succeeding ratchet tooth 24/segment. Upon passing the proximal edge 24*b*, audible feedback may be created.

Proximal movement of the piston rod 4 and, hence of the dose member 5, is prevented due to mechanical cooperation of the pawl means 20, in particular its tip 49, with the proximal edge 24*a* of the respective ratchet tooth 24 of the piston rod 4.

Upon movement of the dose member 5 in the distal direction, the detent 43 passes from the first section 28*a* into the second section 28*b*. Now, rotation of the dose member 5 and, thus, of the piston rod 4 is prevented as the detent 43 cannot override the steep side walls 41*b* of the second section 28*b*. As rotation of the dose member 5 is no longer possible, no further dose of the medication 10 can be set.

As proximal movement of the piston rod 4/the dose member 5 is prevented, the detent 43 also cannot pass from the second section 28*b* back into the first section 28*a* for enabling further rotation of the dose member 5. The device 1 is rotationally and proximally locked.

Distal movement of the dose member 5 and, hence of the piston rod 4, is guided by the detent 43 engaging the second section 28*b*. The dose member 5 and the piston rod 4 are further moved distally until the contact element 19 of the piston rod 4 abuts the axial end stop 18*a* correlating with the size of the set dose, i.e. the specific axial end stop 18*a*. When the contact element 19 abuts the axial end stop 18*a*, the set dose has been completely delivered. Once the contact element 19 abuts the axial end stop 18*a*, further distal movement of the piston rod 4 and of the dose member 5 is prevented. The device 1 is distally locked. Moreover, the rotational stop member 18*c* arranged directly adjacent to the axial end stop 18*a* prevents rotation of the piston rod 4 as previously described. The rotational stop member 18*c* thus provides a rotational end stop in addition to the rotational end stop provided by the second section 28*a* and the detent 43.

In this context it should be noted that the axial guidance of the dose member 5/piston rod 4 during dose delivery and the axial end stop of the dose member 5/piston rod 4 at the end of the dose delivery operation are realized by means of different components, i.e. by means of the body 3 with the detent 43 cooperating with the tracks 27 of the dose member 5 (axial guidance) and by means of the stop member 18 mechanically cooperating with the piston rod 4 (axial end stop).

Figure 8:
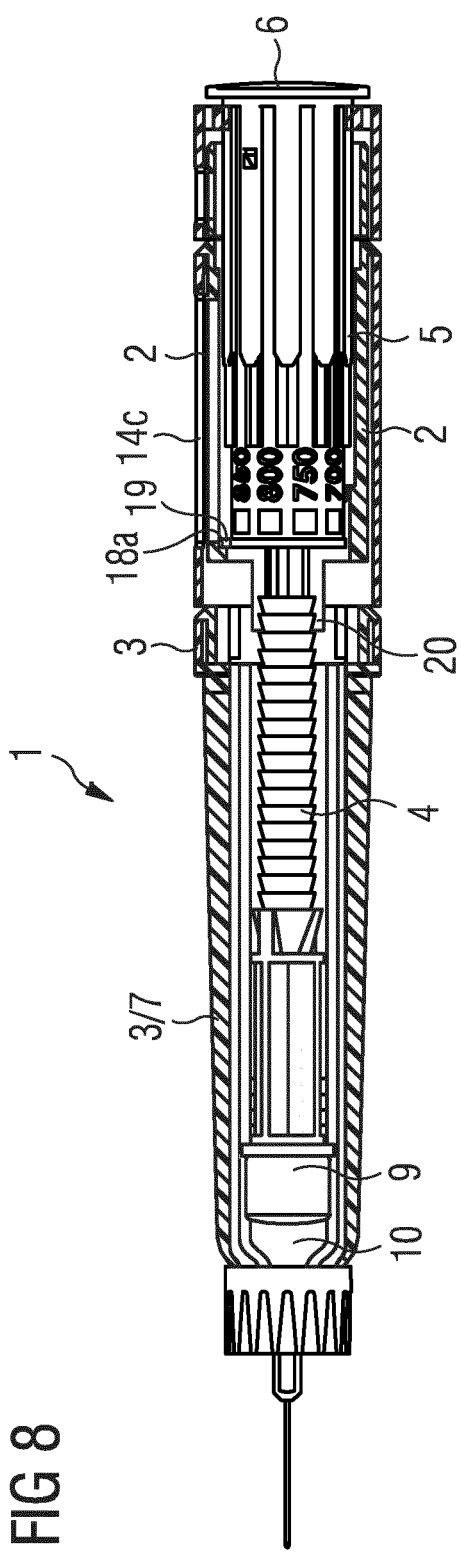

The device 1 is now locked. No further dose of the medication 10 can be set and dispensed from the device 1. This situation is depicted in FIG. 8. The remaining amount of the medication 10 is discarded along with the device 1. The third window aperture 14*c* displays the size of the dose dispensed from the device 1 as well as a color, e.g. the red color for indicating that the dose was correctly set and dispensed. No symbols 38 are displayed through the first and second window aperture 14*a*, 14*b*. Rather, parts of the dose member 5 may be visible through said window apertures 14*a*, 14*b*.

In an alternative embodiment, the staircase of axial end stops 18 could be applied to the tracks in the dose member 5. In that case, each track 27 may have a different wall or end surface 40. Furthermore, the dispensing end stop on the body 3 would be formed by the detent 43. Thus, the interaction member 2 and the piston rod 4 might be simplified (removal of stops member 18 and contact element 19). This embodiment would mean that the tracks 27 and end stops 18 are "reunited" in a series of single features.

In the following, assembly of the medication delivery device 1 is described in connection with FIG. 4.

In a first step, the components of the device 1 as described above are provided.

These components are:
- the needle assembly 13 comprising the needle 12,
- the dose 9,
- the piston rod 4,
- the interaction member 2,
- the dose member 5,
- the end cap 6,
- the body 3.

In an alternative embodiment, the cartridge 8 and, optionally the cartridge holder 7, may be additionally provided for holding the medication 10. In a further embodiment, the piston rod 4 and the dose member 5 constitute one single, e.g. injection molded, component. In a further embodiment, the end cap 6 and the dose member 5 constitute one single, e.g. injection molded, component. Alternatively, the piston rod 4, the dose member 5 and the end cap 6 may comprise one single, e.g. injection molded, component. In a further embodiment, the interaction member 2 and the body 3 constitute one single component. In other words, the structural elements of the interaction member 2 (stop member 18, pawl means 20) may be part of the body 3 and an inner sleeve-member of the body 3 for providing the said structural elements may be superfluous. For the previously mentioned alternative embodiments, the following method steps have to be adapted accordingly.

In a next step, the interaction member 2 is inserted into the body 3. The interaction member 2 may be inserted via the open distal end of the body 3 and may be moved proximally until the coupling elements 15*a*, 29 of the two components are aligned. Then, the mating coupling element 29 of the interaction member 2 snaps into the coupling element 15*a* of the body 3 for rotationally and axially locking the interaction member 2 to the body 3. In the embodiment where the structural parts of the interaction member 2 are arranged on the body 3, this step may be redundant.

In a next step, the piston rod 4 and the dose member 5 are connected to one another due to mechanical cooperation of the engagement features 25, 26. The piston rod 4 and the dose member 5 are now secured against relative axial and rotational movement. In the embodiment where the piston rod 4 and the dose member 5 constitute a single component of the device 1, this step may be redundant.

In a next step, the piston rod 4 and the dose member 5 are inserted into the interaction member 2 and the body 3. The piston rod 4 and the dose member 5 are inserted via the open proximal end of the body 3 and are moved in the distal direction.

When being moved distally, the distal end of the piston rod 4 passes the pawl means 20 which are thereby deflected in the radial outward direction. Upon further distal movement, the recess 20a of the pawl means 20 engages the segments 34 of the first axial region 22a of the piston rod 4, thereby guiding the axial movement of the piston rod 4 and the dose member 5. The piston rod 4 and the dose member 5 and are moved in the distal direction until the tip 49 of the pawl means 20 of the interaction member 2 abuts the plate-like structure 31 of the first axial region 22a of the piston rod 4.

In a next step, the end cap 6 is mounted onto the dose member due to mechanical cooperation of the fixing elements 35, 36. Relative rotational and axial movement of the dose member 5 and the end cap 6 is thus prevented. In the embodiment where the dose member 5 and the end cap 6 constitute a single component of the device 1, this step may be redundant.

In a next step, the cartridge 8 holding the medication 10 or the cartridge holder 7 containing the cartridge 8 may be connected to the body 3. In the embodiment where the device 1 is embodied as a pre-filled syringe, this step may be redundant. Rather, the medication 10 may be contained within the body 3 of the device 1.

Finally, the needle assembly 13 is connected, e.g. screwed, to the distal end of the device 1. The device 1 can now be supplied to the user. When supplied, the device 1 is in the unprimed state and must be primed prior to use as described above.

The scope of protection is not limited to the examples given herein above. The invention is embodied in each novel characteristic and each combination of characteristics, which particularly includes every combination of any features which are stated in the claims, even if this feature or this combination of features is not explicitly stated in the claims or in the examples.

What is claimed is:

1. An assembly for a medication delivery device comprising:
   a body;
   a piston rod adapted and arranged to be rotated with respect to the body for setting a dose of a medication and to be axially moved in a distal direction with respect to the body for delivering the set dose of the medication wherein, when viewed in cross-section, the piston rod comprises a plurality of ratchet teeth adapted and arranged to enable rotation of the piston rod during setting of the dose of the medication and prevent movement of the piston rod in a proximal direction with respect to the body when setting and delivering the dose of the medication; and
   at least one stop member secured against axial and rotational movement with respect to the body, wherein the stop member is adapted and arranged to mechanically cooperate with the piston rod,
   wherein, when setting the dose of the medication, the piston rod becomes aligned with the stop member, and
   wherein, when delivering the set dose, the piston rod is moved in the distal direction towards the stop member, such that the piston rod and the stop member abut at the end of the dose delivery operation, and such that further distal movement of the piston rod is prevented after the set dose of the medication was delivered.
2. The assembly according to claim 1, wherein the ratchet teeth extend circumferentially around the piston rod.
3. The assembly according to claim 1,
   wherein the at least one stop member is configured such that rotation of the piston rod for setting a further dose of the medication is prevented once the stop member and the piston rod abut after delivery of the set dose.
4. The assembly according to claim 1,
   wherein the stop member comprises a staircase of axial end stops.
5. The assembly according to claim 4,
   wherein each axial end stop of the staircase of axial end stops defines the end of a specific track the piston rod is moved along in the distal direction during dose delivery, and
   wherein the piston rod comprises a contact element which is adapted and arranged to mechanically cooperate with a specific axial end stop at the end of the dose delivery operation.
6. The assembly according to claim 5,
   wherein, during dose setting, the piston rod is rotated such that the contact element is brought into axial alignment with the specific axial end stop, and
   wherein an azimuthal and/or axial position of the specific axial end stop with respect to the body is correlated with a size of the set dose.
7. The assembly according to claim 5,
   wherein the stop member further comprises an axial priming stop,
   wherein, before the assembly is primed, the contact element is axially aligned with the axial priming stop, and
   wherein, during priming, the contact element is moved axially towards the axial priming stop.
8. The assembly according to claim 5,
   wherein the piston rod comprises a first axial region, a second axial region and a third axial region passing over into one another as seen along a longitudinal axis of the assembly,
   wherein the ratchet teeth are arranged in the second axial region, and
   wherein the contact element is arranged in the third axial region.
9. The assembly according to claim 4,
   wherein the stop member comprises a plurality of rotational end stops extending at least partly along a longitudinal axis of the assembly, and
   wherein adjacent axial end stops are connected by one respective rotational end stop.
10. The assembly according to claim 1, further comprising:
    an interaction member secured against axial and rotational movement with respect to the body,
    wherein the interaction member comprises the at least one stop member, and
    wherein the at least one stop member is helically arranged on an inner surface of the interaction member.
11. The assembly according to claim 1, further comprising:
    wherein the at least one pawl means and the piston rod are configured to mechanically cooperate with one another such that, in an unprimed state of the assembly, rotation of the piston rod with respect to the body for performing a dose setting operation is prevented.
12. The assembly according to claim 11,
    wherein the piston rod comprises an anti-rotation member,
    wherein, in the unprimed state, the at least one pawl means engages the anti-rotation member such that rotational movement of the piston rod for setting the dose of the medication is prevented, and wherein, for priming the assembly, the piston rod is moved in the distal direction such that the at least one pawl means and the anti-rotation member are brought out of engagement for enabling rotation of the piston rod for setting the dose of the medication.

13. The assembly according to claim 11,
wherein the stop member comprises an axial priming stop, and
wherein, at the end of a priming operation, the piston rod abuts the axial priming stop such that further distal movement of the piston rod with respect to the body for priming the assembly is prevented.

14. The assembly according to claim 11, wherein the at least one pawl means is adapted and arranged to mechanically cooperate with the ratchet teeth to provide an audible feedback when the set dose is dispensed.

15. The assembly according to claim 1,
wherein each ratchet tooth comprises a distal edge and a proximal edge,
wherein the proximal edge extends perpendicular to a longitudinal axis of the assembly, and
wherein the distal edge is oblique with respect to the longitudinal axis of the assembly.

16. The assembly according to claim 1, further comprising:
an interaction member secured against axial and rotational movement with respect to the body,
wherein the interaction member comprises the at least one stop member and pawl means which are configured to mechanically cooperate with the piston rod.

17. A medication delivery device comprising an assembly having:
a body;
a piston rod adapted and arranged to be rotated with respect to the body for setting a dose of a medication and to be axially moved in a distal direction with respect to the body for delivering the set dose of the medication wherein, when viewed in cross-section, the piston rod comprises a plurality of ratchet teeth adapted and arranged to enable rotation of the piston rod during setting of the dose of the medication and prevent movement of the piston rod in a proximal direction with respect to the body when setting and delivering the dose of the medication; and
at least one stop member secured against axial and rotational movement with respect to the body, wherein the stop member is adapted and arranged to mechanically cooperate with the piston rod,
wherein, when setting the dose of the medication, the piston rod becomes aligned with the stop member,
wherein, when delivering the set dose, the piston rod is moved in the distal direction towards the stop member, such that the piston rod and the stop member abut at the end of the dose delivery operation, and such that further distal movement of the piston rod is prevented after the set dose of the medication was delivered, and
wherein the medication delivery device is a single-shot variable-dose device.

18. An assembly for a medication delivery device comprising:
a body;
a piston rod adapted and arranged to be rotated with respect to the body for setting a dose of a medication and to be axially moved in a distal direction with respect to the body for delivering the set dose of the medication wherein, when viewed in cross-section, the piston rod comprises a plurality of ratchet teeth adapted and arranged to enable rotation of the piston rod during setting of the dose of the medication, and
at least one stop member secured against axial and rotational movement with respect to the body, wherein the stop member is adapted and arranged to mechanically cooperate with the piston rod,
wherein, when setting the dose of the medication, the piston rod becomes aligned with the stop member,
wherein, when delivering the set dose, the piston rod is moved in the distal direction towards the stop member, such that the piston rod and the stop member abut at the end of the dose delivery operation, and such that further distal movement of the piston rod is prevented after the set dose of the medication was delivered,
wherein each respective ratchet tooth of the plurality of ratchet teeth comprises a distal edge and a proximal edge,
wherein the proximal edge extends perpendicular to a longitudinal axis of the assembly, and
wherein the distal edge is oblique with respect to the longitudinal axis of the assembly.

19. An assembly for a medication delivery device comprising:
a body;
a piston rod adapted and arranged to be rotated with respect to the body for setting a dose of a medication and to be axially moved in a distal direction with respect to the body for delivering the set dose of the medication wherein, when viewed in cross-section, the piston rod comprises a plurality of ratchet teeth adapted and arranged to enable rotation of the piston rod during setting of the dose of the medication;
at least one pawl means secured against axial and rotational movement with respect to the body adapted and arranged to mechanically cooperate with the ratchet teeth to prevent movement of the piston rod in a proximal direction with respect to the body when setting and delivering the dose of the medication; and
at least one stop member secured against axial and rotational movement with respect to the body, wherein the stop member is adapted and arranged to mechanically cooperate with the piston rod,
wherein, when setting the dose of the medication, the piston rod becomes aligned with the stop member, and
wherein, when delivering the set dose, the piston rod is moved in the distal direction towards the stop member, such that the piston rod and the stop member abut at the end of the dose delivery operation, and such that further distal movement of the piston rod is prevented after the set dose of the medication was delivered.

20. A medication delivery device comprising an assembly having:
a body;
a piston rod adapted and arranged to be rotated with respect to the body for setting a dose of a medication and to be axially moved in a distal direction with respect to the body for delivering the set dose of the medication wherein, when viewed in cross-section, the piston rod comprises a plurality of ratchet teeth adapted and arranged to enable rotation of the piston rod during setting of the dose of the medication,
at least one pawl means secured against axial and rotational movement with respect to the body adapted and arranged to mechanically cooperate with the ratchet teeth to prevent movement of the piston rod in a proximal direction with respect to the body when setting and delivering the dose of the medication, and at least one stop member secured against axial and rotational movement with respect to the body, wherein the stop member is adapted and arranged to mechanically cooperate with the piston rod, wherein, when setting the dose of the medication, the piston rod becomes aligned with the stop member, wherein, when delivering the set dose, the piston rod is moved in the distal direction towards the stop member, such that the piston rod and the stop member abut at the end of the dose delivery operation, and such that further distal movement of the piston rod is prevented after the set dose of the medication was delivered, and wherein the medication delivery device is a single-shot variable-dose device.

* * * * *